United States Patent
Higano et al.

(10) Patent No.: US 11,966,112 B2
(45) Date of Patent: Apr. 23, 2024

(54) DETECTION APPARATUS

(71) Applicant: Japan Display Inc., Tokyo (JP)

(72) Inventors: Toshiyuki Higano, Minato-ku (JP); Kazuhiro Nishiyama, Minato-ku (JP); Genki Asozu, Minato-ku (JP); Kazuki Matsunaga, Minato-ku (JP)

(73) Assignee: Japan Display Inc., Tokyo (JP)

( * ) Notice: Subject to any disclaimer, the term of this patent is extended or adjusted under 35 U.S.C. 154(b) by 189 days.

(21) Appl. No.: 17/453,224

(22) Filed: Nov. 2, 2021

(65) Prior Publication Data

US 2022/0057664 A1 Feb. 24, 2022

Related U.S. Application Data

(63) Continuation of application No. PCT/JP2020/015785, filed on Apr. 8, 2020.

(30) Foreign Application Priority Data

May 8, 2019 (JP) ................. 2019-088580

(51) Int. Cl.
*G02F 1/1333* (2006.01)
*G02F 1/1335* (2006.01)
(Continued)

(52) U.S. Cl.
CPC .... *G02F 1/13338* (2013.01); *G02F 1/133514* (2013.01); *G06V 40/1318* (2022.01); *A61B 5/1172* (2013.01); *A61B 5/489* (2013.01)

(58) Field of Classification Search
CPC .......... G02F 1/13338; G02F 1/133514; G06V 40/1318
(Continued)

(56) References Cited

U.S. PATENT DOCUMENTS

2012/0249504 A1\* 10/2012 Kim ................. G06F 3/042
345/207
2015/0138640 A1 5/2015 Matsushita
(Continued)

FOREIGN PATENT DOCUMENTS

CN 109709700 A 5/2019
JP 2015-099239 A 5/2015
(Continued)

OTHER PUBLICATIONS

International Search Report dated Jun. 9, 2020 in PCT/JP2020/015785 filed on Apr. 8, 2020, 5 pages (with English Translation).

*Primary Examiner* — Charles S Chang
(74) *Attorney, Agent, or Firm* — Maier & Maier, PLLC

(57) ABSTRACT

According to an aspect, a detection apparatus includes: an optical sensor including a sensor base member and a plurality of photoelectric conversion elements that are provided on the sensor base member and each of which is configured to output a signal corresponding to light emitted to the photoelectric conversion element; and a lighting device including a plurality of first light-emitting elements configured to emit first light having a first maximum emission wavelength and a plurality of second light-emitting elements configured to emit second light having a second maximum emission wavelength. Each of the photoelectric conversion elements has responsivity in a wavelength region including a wavelength region of the first light and a wavelength region of the second light.

11 Claims, 25 Drawing Sheets

(51) Int. Cl.
*G06V 40/13* (2022.01)
*A61B 5/00* (2006.01)
*A61B 5/1172* (2016.01)

(58) Field of Classification Search
USPC .......................................................... 349/12
See application file for complete search history.

(56) References Cited

U.S. PATENT DOCUMENTS

| | | |
|---|---|---|
| 2017/0065177 A1 | 3/2017 | Sugi et al. |
| 2018/0268190 A1 | 9/2018 | Chung et al. |
| 2018/0270403 A1 | 9/2018 | Chung et al. |
| 2018/0349673 A1 | 12/2018 | Lin et al. |
| 2018/0358401 A1* | 12/2018 | Lin et al. |
| 2019/0034020 A1* | 1/2019 | He .................... H10K 59/12 |
| 2019/0095677 A1 | 3/2019 | Chung et al. |
| 2022/0043999 A1* | 2/2022 | Huang ............ G06V 40/1318 |

FOREIGN PATENT DOCUMENTS

| | | |
|---|---|---|
| JP | 2016-164787 A | 9/2016 |
| JP | 2017-051339 A | 3/2017 |

* cited by examiner

DETECTION APPARATUS

CROSS-REFERENCE TO RELATED APPLICATION

This application claims the benefit of priority from Japanese Patent Application No. 2019-088580 filed on May 8, 2019 and International Patent Application No. PCT/JP2020/015785 filed on Apr. 8, 2020, the entire contents of which are incorporated herein by reference.

BACKGROUND

1. Technical Field

What is disclosed herein relates to a detection apparatus.

2. Description of the Related Art

Japanese Patent Application Laid-open Publication No. 2016-164787 (JP-A-2016-164787) describes a vein image capturing apparatus for capturing a vein image. The vein image capturing apparatus includes a light emitter, a light receiver, a light-blocking layer, and a cover glass. Near-infrared light is emitted from the light emitter to a living body placed on the cover glass, and reflected light from the living body is received by the light receiver. Thus, the vein image capturing apparatus can capture the vein image of the living body.

Detection apparatuses provided with an optical sensor are required to detect not only the vein image, but also various types of biological information on an object to be detected, such as a fingerprint. In this case, the optical sensor needs to include a light source for emitting light having a plurality of different wavelengths. For example, by irradiating the living body with the near-infrared light when the vein image is detected, and irradiating the living body with visible light when the fingerprint is detected, it is possible to detect various types of biological information. JP-A-2016-164787 does not describe a configuration of the vein image capturing apparatus for detecting the various types of biological information using the same device.

SUMMARY

According to an aspect, a detection apparatus includes: an optical sensor including a sensor base member and a plurality of photoelectric conversion elements that are provided on the sensor base member and each of which is configured to output a signal corresponding to light emitted to the photoelectric conversion element; and a lighting device including a plurality of first light-emitting elements configured to emit first light having a first maximum emission wavelength and a plurality of second light-emitting elements configured to emit second light having a second maximum emission wavelength. Each of the photoelectric conversion elements has responsivity in a wavelength region including a wavelength region of the first light and a wavelength region of the second light.

According to an aspect, a detection apparatus includes: a liquid crystal display panel including an array substrate, a counter substrate facing the array substrate, and a liquid crystal layer provided between the array substrate and the counter substrate; an optical sensor including a sensor base member and a plurality of photoelectric conversion elements that are provided on the sensor base member and each of which is configured to output a signal corresponding to light emitted to the photoelectric conversion element; and a lighting device including a plurality of first light-emitting elements configured to emit first light having a first maximum emission wavelength and a plurality of second light-emitting elements configured to emit second light having a second maximum emission wavelength. Each of the photoelectric conversion elements has responsivity in a wavelength region including a wavelength region of the first light and a wavelength region of the second light. The first light-emitting elements and the second light-emitting elements are configured to emit the first light and the second light at respective different wavelengths in a time-division manner.

According to an aspect, a detection apparatus includes: a liquid crystal display panel including an array substrate, a counter substrate facing the array substrate, and a liquid crystal layer provided between the array substrate and the counter substrate; an optical sensor including a sensor base member, a plurality of first photoelectric conversion elements, and a second photoelectric conversion element, the first photoelectric conversion elements and the second photoelectric conversion element provided on the sensor base member and having responsivity in different wavelength regions, and each of the first photoelectric conversion elements and the second photoelectric conversion element configured to receive light and output a signal corresponding to the received light; and a plurality of light-emitting elements configured to have a light emission intensity over a wavelength region in which the first photoelectric conversion elements have responsivity and a wavelength region in which the second photoelectric conversion element has responsivity. The first photoelectric conversion elements and a plurality of the second photoelectric conversion elements are configured to receive light in the wavelength regions different from each other during the same detection period.

DETAILED DESCRIPTION

Figure 1:
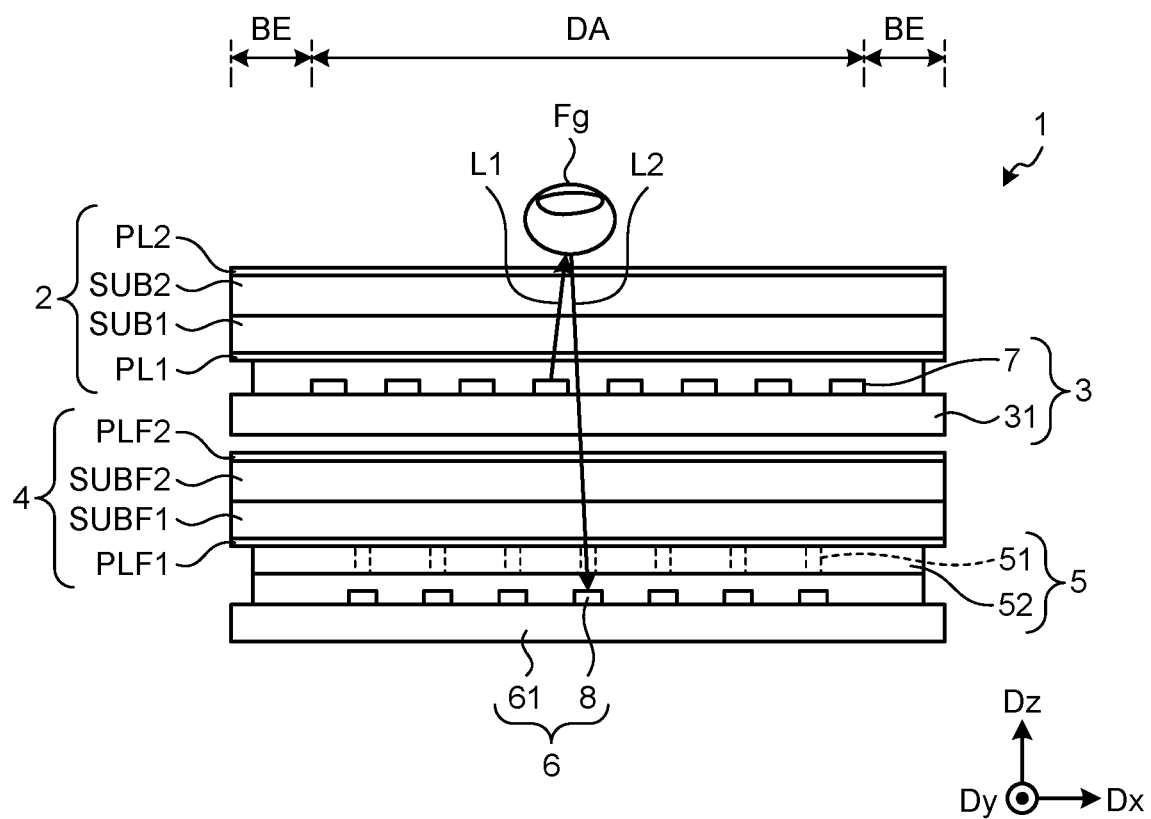
FIG. 1 is a sectional view illustrating a schematic sectional configuration of a detection apparatus according to a first embodiment.

The following describes modes (embodiments) for carrying out the present disclosure in detail with reference to the drawings. The present disclosure is not limited to the description of the embodiments given below. Components described below include those easily conceivable by those skilled in the art or those substantially identical thereto. Moreover, the components described below can be appropriately combined. The disclosure is merely an example, and the present disclosure naturally encompasses appropriate modifications easily conceivable by those skilled in the art while maintaining the gist of the disclosure. To further clarify the description, the drawings schematically illustrate, for example, widths, thicknesses, and shapes of various parts as compared with actual aspects thereof, in some cases. However, they are merely examples, and interpretation of the present disclosure is not limited thereto. The same element as that illustrated in a drawing that has already been discussed is denoted by the same reference numeral through the description and the drawings, and detailed description thereof will not be repeated in some cases where appropriate.

In this disclosure, when an element is described as being "on/upon" another element, the element can be directly on the other element, or there can be one or more elements between the element and the other element.

First Embodiment

FIG. 1 is a sectional view illustrating a schematic sectional configuration of a detection apparatus according to a first embodiment. As illustrated in FIG. 1, a detection apparatus 1 includes a display panel 2, a lighting device 3, a wavelength selection filter 4, an optical element 5, and an optical sensor 6. The optical sensor 6, the optical element 5, the wavelength selection filter 4, the lighting device 3, and the display panel 2 are stacked in a third direction Dz in the order as listed.

A first direction Dx and a second direction Dy are directions parallel to a surface of a sensor base member 61 serving as a base member of the optical sensor 6. The first direction Dx is orthogonal to the second direction Dy. The first direction Dx may, however, intersect the second direction Dy without being orthogonal thereto. The third direction Dz is a direction orthogonal to the first direction Dx and the second direction Dy. The third direction Dz corresponds to, for example, a direction normal to the sensor base member 61. Hereinafter, the term "plan view" refers to a positional relation as viewed from the third direction Dz.

The display panel 2 has a display area DA and a peripheral area BE. The display area DA is an area that includes a plurality of pixels PX (refer to FIG. 2) and displays an image. The peripheral area BE is an area not overlapping the pixels PX, and is disposed outside the display area DA.

The display panel 2 is a liquid crystal display panel including a liquid crystal layer LC (refer to FIG. 3) as a display element. The display panel 2 includes an array substrate SUB1, a counter substrate SUB2, a first polarizing plate PL1, and a second polarizing plate PL2. The array substrate SUB1 includes a first substrate 21 (refer to FIG. 3), the pixels PX, and a drive circuit 120 (refer to FIG. 2). For example, the first substrate 21, a plurality of transistors, a plurality of capacitors, and various types of wiring constitute the array substrate SUB1 for driving the pixels PX. The array substrate SUB1 is a drive circuit substrate and is also called a "backplane" or an "active matrix substrate".

The lighting device 3 includes a light source base member 31 and a plurality of light-emitting elements 7. The lighting device 3 is provided so as to face the array substrate SUB1 and is provided between the display panel 2 and the optical sensor 6 in the third direction Dz. More specifically, the lighting device 3 is provided between the display panel 2 and the wavelength selection filter 4 in the third direction Dz. The light source base member 31 is a light-transmitting insulating base material, such as a glass substrate. The light source base member 31 may alternatively be a resin substrate or a resin film formed of a resin such as polyimide.

The light-emitting elements 7 are provided on a surface of the light source base member 31, the surface facing the display panel 2. The light-emitting elements 7 are inorganic light-emitting diode (LED) elements and emit light L1 toward the display panel 2.

The wavelength selection filter 4 is provided between the optical sensor 6 and both the lighting device 3 and the display panel 2 in the third direction Dz. The wavelength selection filter 4 is provided on a light incidence surface side of a plurality of photoelectric conversion elements 8 and faces the photoelectric conversion elements 8. The wavelength selection filter 4 includes a filter array substrate SUBF1, a filter counter substrate SUBF2, a first polarizing plate PLF1, and a second polarizing plate PLF2. The wavelength selection filter 4 has a configuration similar to that of the display panel 2 and includes a liquid crystal layer LCA (refer to FIG. 9) between the filter array substrate SUBF1 and the filter counter substrate SUBF2. Light L2 reflected on a surface of or in a finger Fg is changed in polarization state by the liquid crystal layer LCA. The wavelength selection filter 4 controls a phase difference δ of the liquid crystal layer LCA, and thereby can vary a transmission band for transmitting the light L2 and a non-transmission band for not transmitting the light L2.

The optical element 5 is provided between the optical sensor 6 and both the lighting device 3 and the display panel 2, more specifically, between the optical sensor 6 and the wavelength selection filter 4 in the third direction Dz. The optical element 5 has a flat plate shape and is provided in an area overlapping at least the photoelectric conversion elements 8. The optical element 5 includes light-transmitting areas 51 and a non-light-transmitting area 52. The light-transmitting areas 51 are provided so as to penetrate the optical element 5 in a thickness direction thereof in positions overlapping the respective photoelectric conversion elements 8. The light-transmitting areas 51 have a light-transmitting property and transmit the light L2 incident on the photoelectric conversion elements 8. The non-light-transmitting area 52 is provided between the light-transmitting areas 51 and has lower light transmittance than that of the light-transmitting areas 51. That is, the light L2 does not pass through the non-light-transmitting area 52.

The optical sensor 6 includes the sensor base member 61 and the photoelectric conversion elements 8. The sensor base member 61 is an insulating base material, such a glass substrate. The sensor base member 61 may alternatively be a resin substrate or a resin film formed of a resin such as polyimide. The optical sensor 6 is provided so as to face the array substrate SUB1, and the photoelectric conversion elements 8 are provided on a surface on the display panel 2 side of the sensor base member 61. The photoelectric conversion elements 8 are provided in an area of the sensor base member 61 overlapping the display area DA. The photoelectric conversion elements 8 may, however, be provided in an area overlapping a part of the display area DA.

The photoelectric conversion elements 8 are, for example, photodiodes formed of, for example, amorphous silicon. Each of the photoelectric conversion elements 8 outputs, to a detection circuit 163 (refer to FIG. 15), an electrical signal corresponding to the light L2 emitted thereto.

With the above-described configuration, the light L1 emitted from the light-emitting elements 7 is incident on the display panel 2. The light L1 passes through the display panel 2 and is reflected on the surface of or in the finger Fg. The light L2 reflected by the finger Fg passes through the display panel 2 and the lighting device 3 and is incident on the wavelength selection filter 4. The wavelength selection filter 4 transmits light of the light L2 having a wavelength component in the transmission band. The light L2 having passed through the wavelength selection filter 4 passes through the light-transmitting areas 51 of the optical element 5 and is incident on the photoelectric conversion elements 8. As a result, the optical sensor 6 can detect biological information such as a fingerprint and a blood vessel image (vein pattern) of the finger Fg based on the light L2. During display, the display panel 2 can display the image using the light L1 having passed through the display panel 2. In this manner, the light-emitting elements 7 serve as both a light source for detection and a light source for display.

Figure 2:
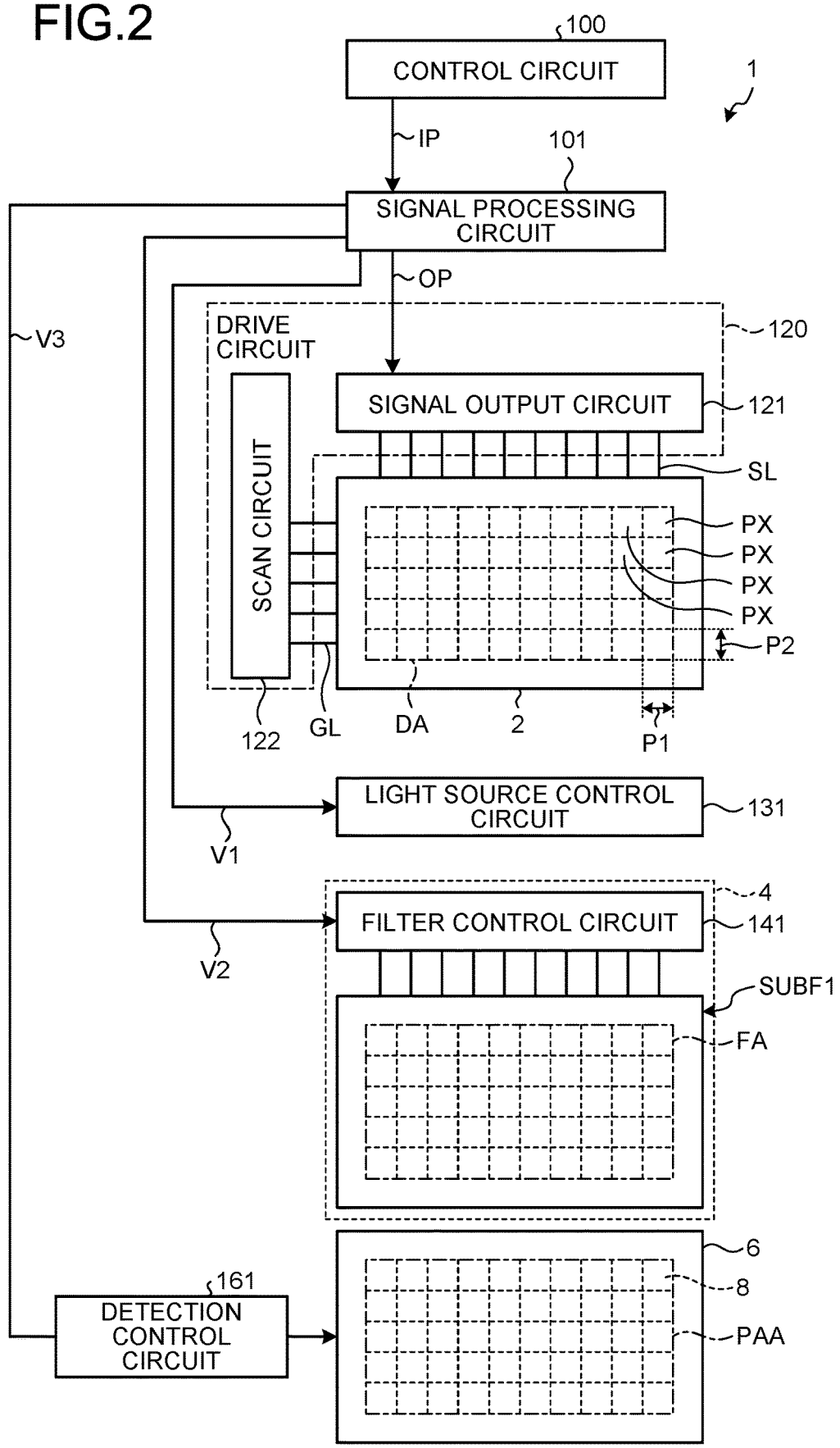
FIG. 2 is an explanatory diagram illustrating a main configuration example of the detection apparatus according to the first embodiment.

FIG. 2 is an explanatory diagram illustrating a main configuration example of the detection apparatus according to the first embodiment. The detection apparatus 1 further includes a control circuit 100, a signal processing circuit 101, the drive circuit 120, a light source control circuit 131, a filter control circuit 141, and a detection control circuit 161.

The control circuit 100 is a circuit that controls the display and the detection of the biological information performed by the detection apparatus 1. The signal processing circuit 101 outputs various signals based on an input signal IP received from the control circuit 100. The input signal IP includes a signal (for example, a red-green-blue (RGB) image signal) for displaying the image and a signal for controlling the detection. During the display, the signal processing circuit 101 generates an image signal OP based on the input signal IP. The signal processing circuit 101 outputs the image signal OP to each of the pixels PX through the drive circuit 120. The signal processing circuit 101 is an integrated circuit such as a field-programmable gate array (FPGA).

The display panel 2 includes the pixels PX, and the pixels PX are arranged in the first direction Dx and the second direction Dy in the display area DA. The drive circuit 120 includes a signal output circuit 121 and a scan circuit 122. The signal output circuit 121 and the scan circuit 122 are provided in the peripheral area BE. The scan circuit 122 is a circuit that drives a plurality of scan lines GL based on various control signals from the signal processing circuit 101. The scan circuit 122 sequentially or simultaneously selects the scan lines GL, and supplies a gate drive signal to each of the selected scan lines GL. By this operation, the scan circuit 122 selects the pixels PX coupled to the scan lines GL. The signal output circuit 121 outputs the image signals OP to the selected pixels PX through pixel signal lines SL.

The signal processing circuit 101 generates a light source control signal V1, a filter control signal V2, and a detection control signal V3 based on the input signal IP. The signal processing circuit 101 outputs the light source control signal V1 to the light source control circuit 131. The light source control circuit 131 is a circuit for controlling the lighting of the light-emitting elements 7 of the lighting device 3. The light source control circuit 131 controls to turn on and off each of the light-emitting elements 7 based on the light source control signal V1.

The signal processing circuit 101 outputs the filter control signal V2 to the filter control circuit 141. The filter control circuit 141 controls the transmission band and the non-transmission band of the wavelength selection filter 4. The filter array substrate SUBF1 of the wavelength selection filter 4 is provided with a plurality of unit filter areas FA. The unit filter areas FA are provided in positions overlapping the display area DA in the plan view. The filter control circuit 141 can change the transmission band of light for each of the unit filter areas FA, or can change the transmission band of light for all the unit filter areas FA. Arrangement pitches of the unit filter areas FA may be equal to arrangement pitches P1 and P2 of the pixels PX, or may be greater than the arrangement pitches P1 and P2.

The signal processing circuit 101 outputs the detection control signal V3 to the detection control circuit 161. The detection control circuit 161 controls the detection of the light L2 performed by the photoelectric conversion elements 8 of the optical sensor 6. The optical sensor 6 is provided with a plurality of partial detection areas PAA. The partial detection areas PAA are provided in positions overlapping the unit filter areas FA and the display area DA. Each of the photoelectric conversion elements 8 is provided for a corresponding one of the partial detection areas PAA, and the detection control circuit 161 controls the detection of the light L2 performed by the photoelectric conversion element 8 for each of the partial detection area PAA. Arrangement pitches of the partial detection areas PAA may be equal to the arrangement pitches P1 and P2 of the pixels PX, or may be greater than the arrangement pitches P1 and P2.

The control circuit 100, the signal processing circuit 101, the light source control circuit 131, the filter control circuit 141, and the detection control circuit 161 may each be made up of an individual integrated circuit (IC), or may collectively be made up of one IC. Each of the ICs may be mounted as a chip on film (COF) on a flexible printed circuit board or a rigid substrate coupled to a corresponding one of the array substrate SUB1, the filter array substrate SUBF1, the light source base member 31, and the sensor base member 61. The present disclosure is not limited thereto. Each of the ICs may be mounted as a chip on glass (COG) in a peripheral area of a corresponding one of the array substrate SUB1, the filter array substrate SUBF1, the light source base member 31, and the sensor base member 61.

During a display period TA, the light-emitting elements 7 emit visible light (for example, white light) toward the display area DA of the display panel 2 based on the light source control signal V1. By this operation, the lighting device 3 serves as a backlight of the display panel 2. During the display, the filter control circuit 141 places all the unit filter areas FA in a non-transmitting state based on the filter control signal V2. As a result, the light L2 is blocked by the wavelength selection filter 4 to be restrained from being incident on the photoelectric conversion elements 8. During the display, the detection control circuit 161 stops the detection of the light L2 performed by the photoelectric conversion elements 8. The filter control circuit 141 and the detection control circuit 161 may perform the detection during the display period TA.

During a non-display period TB, the light-emitting elements 7 emit the light L1 (for example, the visible light and near-infrared light) having different wavelengths toward the display panel 2 based on the light source control signal V1. The wavelengths of the light L1 are determined depending on the biological information (such as the fingerprint and the blood vessel image (vein pattern)) to be detected. During the non-display period TB, the filter control circuit 141 sets the transmission band and the non-transmission band of the unit filter areas FA of the wavelength selection filter 4 so as to transmit a wavelength region of the light L2 reflected by the finger Fg. The detection control circuit 161 performs the detection for each beam of the light L2 having a different wavelength. By this operation, the detection apparatus 1 can detect the various types of biological information using one device.

Figure 3:
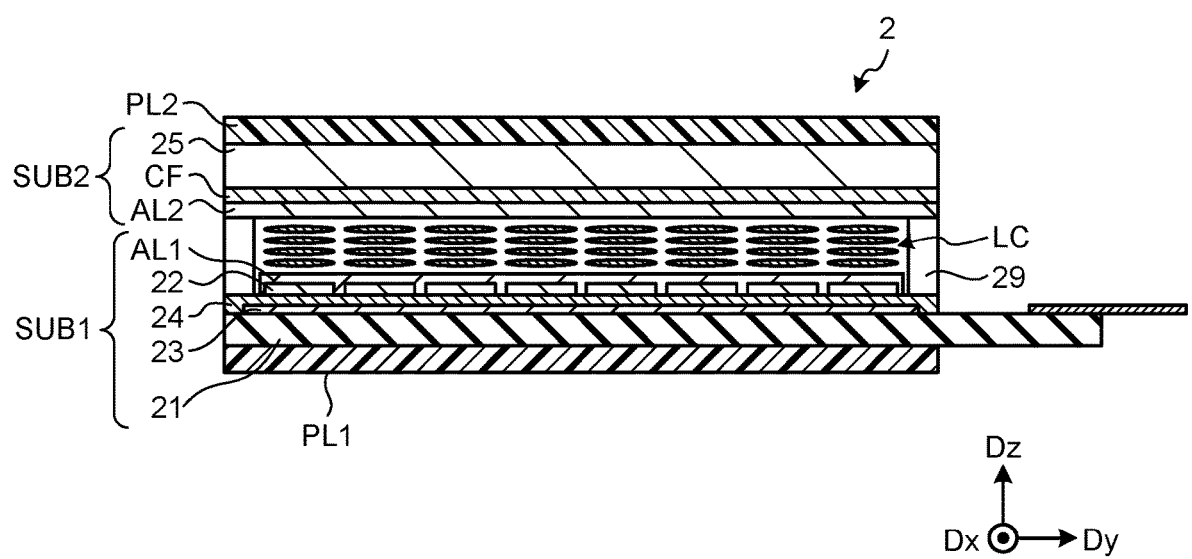
FIG. 3 is a sectional view illustrating a schematic sectional configuration of a display panel.

The following describes detailed configurations of the display panel 2, the lighting device 3, the wavelength selection filter 4, the optical element 5, and the optical sensor 6. FIG. 3 is a sectional view illustrating a schematic sectional configuration of the display panel. As illustrated in FIG. 3, the counter substrate SUB2 is disposed so as to face the array substrate SUB1 in a direction orthogonal to a surface thereof. The liquid crystal layer LC is provided between the array substrate SUB1 and the counter substrate SUB2. The array substrate SUB1 includes the first substrate 21 as a base member. The counter substrate SUB2 includes a second substrate 25 as a base member. The first substrate 21 and the second substrate 25 are formed of, for example, a light-transmitting material such as a glass substrate or a resin substrate.

The array substrate SUB1 includes, for example, pixel electrodes 22, a common electrode 23, an insulating film 24, and a first orientation film AL1 on a side of the first substrate 21 facing the counter substrate SUB2.

Herein, in a direction orthogonal to the first substrate 21, a direction from the first substrate 21 toward the second substrate 25 will be referred to as "upper side" or simply as "above/upon", and a direction from the second substrate 25 toward the first substrate 21 will be referred to as "lower side" or simply as "below".

The common electrode 23 is provided upon the first substrate 21. The common electrode 23 is continuously provided over the display area DA. The common electrode 23 is, however, not limited to this configuration and may be provided with slits and divided into a plurality of pieces. The common electrode 23 is covered with the insulating film 24.

The pixel electrodes 22 are provided upon the insulating film 24 and face the common electrode 23 with the insulating film 24 interposed therebetween. The pixel electrodes 22 and the common electrode 23 are formed of, for example, a light-transmitting conductive material such as indium tin oxide (ITO) or indium zinc oxide (IZO). The insulating film 24 is formed of, for example, a light-transmitting inorganic material such as a silicon oxide or a silicon nitride. The pixel electrodes 22 and the insulating film 24 are covered with the first orientation film AL1.

The counter substrate SUB2 includes, for example, a color filter CF and a second orientation film AL2 on a side of the second substrate 25 facing the array substrate SUB1. The color filter CF is located on the side of the second substrate 25 facing the array substrate SUB1. In one example, the color filter CF includes color filters CFR, CFG, and CFB for displaying different colors, which are formed of resin materials colored in red, green, and blue, respectively.

The second orientation film AL2 is located on a side of the color filter CF facing the array substrate SUB1. The first orientation film AL1 and the second orientation film AL2 are formed of, for example, a material that exhibits a horizontal orientation property The first polarizing plate PL1 is disposed on an external surface of the first substrate 21, or a surface of the first substrate 21 facing the lighting device 3 (refer to FIG. 1). The second polarizing plate PL2 is disposed on an external surface of the second substrate 25, or a surface on an observation position side of the second substrate 25. A first polarization axis of the first polarizing plate PL1 and a second polarization axis of the second polarizing plate PL2 are in a positional relation of, for example, crossed Nicols in an XY-plane. The display panel 2 may include other optical functional elements, such as a retardation film, in addition to the first polarizing plate PL1 and the second polarizing plate PL2.

The array substrate SUB1 and the counter substrate SUB2 are arranged such that the first orientation film AL1 and the second orientation film AL2 face each other. The liquid crystal layer LC is enclosed in a space surrounded by the first orientation film AL1, the second orientation film AL2, and a sealing part 29. The liquid crystal layer LC is formed of a negative liquid crystal material having a negative dielectric anisotropy or a positive liquid crystal material having a positive dielectric anisotropy.

For example, when the liquid crystal layer LC is a negative liquid crystal material and no voltage is applied to the liquid crystal layer LC, a long axis of a liquid crystal molecule is initially oriented in a direction along the first direction Dx in the XY-plane. In contrast, when a voltage is applied to the liquid crystal layer LC, that is, during an on time when an electric field is formed between the pixel electrodes 22 and the common electrode 23, the orientation state of the liquid crystal molecule changes under the influence of the electric field. During the on time, the polarization state of linearly polarized incident light changes according to the orientation state of the liquid crystal molecule when the light passes through the liquid crystal layer LC.

Figure 4:
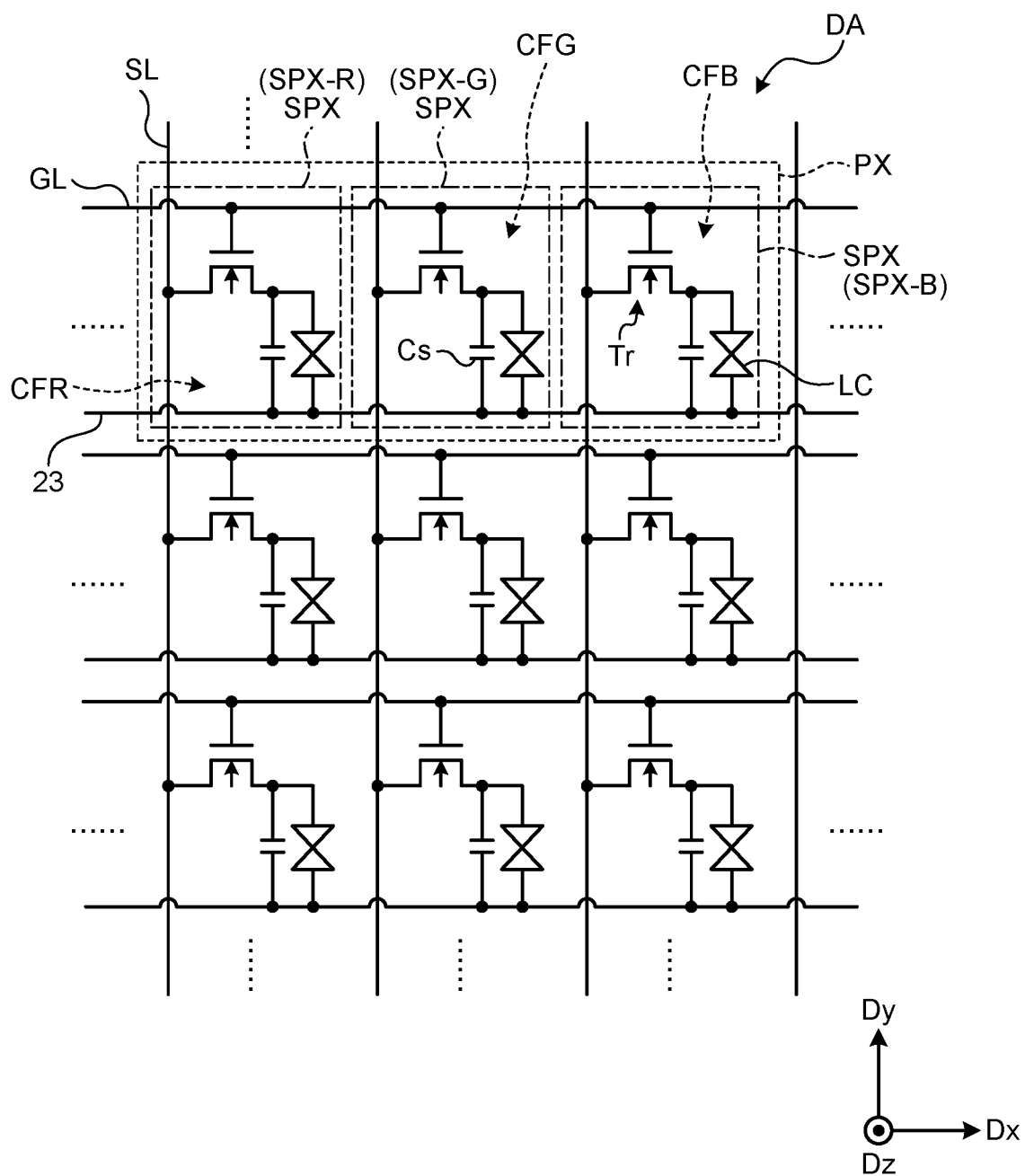
FIG. 4 is a circuit diagram illustrating a pixel array in a display area.

FIG. 4 is a circuit diagram illustrating a pixel array in the display area. For example, the array substrate SUB1 is provided with switching elements Tr of respective sub-pixels SPX, the pixel signal lines SL, and the scan lines GL illustrated in FIG. 4. The pixel signal lines SL extend in the second direction Dy. The pixel signal lines SL are wiring for supplying a pixel signal to each of the pixel electrodes 22 (refer to FIG. 3). The scan lines GL extend in the first direction Dx. The scan lines GL are wiring for supplying a drive signal (scan signal) for driving each of the switching elements Tr.

Each of the pixels PX includes the sub-pixels SPX. Each of the sub-pixels SPX includes the switching element Tr and a capacitance of the liquid crystal layer LC. The switching element Tr includes a thin-film transistor, and in this example, an n-channel metal-oxide-semiconductor (MOS) thin-film transistor (TFT). The insulating film 24 is provided between the pixel electrodes 22 and the common electrode 23 illustrated in FIG. 3, and these components provide a storage capacitor Cs illustrated in FIG. 4.

Color regions colored in three colors of, for example, red (R), green (G), and blue (B) are periodically arranged in the color filters CFR, CFG, and CFB. The color regions of the three colors of R, G, and B are associated with sub-pixels SPX-R, SPX-G, and SPX-B as one set. The sub-pixels SPX corresponding to the color regions of the three colors constitute the pixel PX as one set. The color filter may include color regions of four or more colors. In this case, each pixel PX may include four or more of the sub-pixels SPX.

Figure 5:
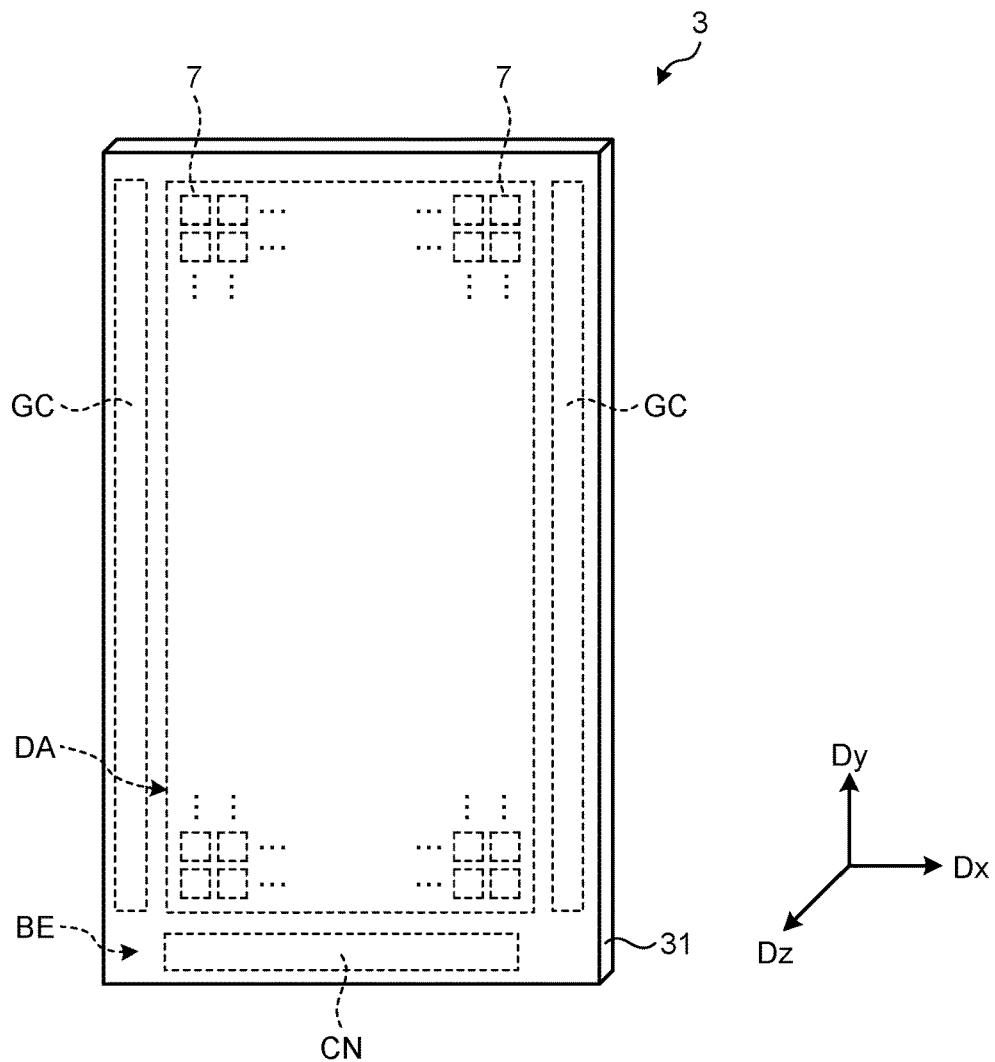
FIG. 5 is a perspective view schematically illustrating a lighting device included in the detection apparatus according to the first embodiment.

FIG. 5 is a perspective view schematically illustrating the lighting device included in the detection apparatus according to the first embodiment. As illustrated in FIG. 5, the light-emitting elements 7 are arranged in an area of the light source base member 31 overlapping the display area DA. The light-emitting elements 7 are arranged in the first direction Dx and the second direction Dy. Peripheral circuits GC for driving the light-emitting elements 7 and coupling terminals CN are disposed in the peripheral area BE.

Figure 6:
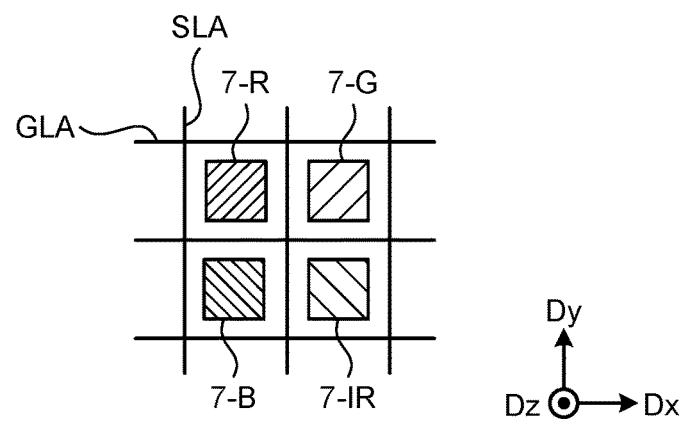
FIG. 6 is a plan view illustrating a plurality of light-emitting elements.

The light source base member 31 is provided with light source scan lines GLA and light source signal lines SLA (refer to FIG. 6). The light-emitting elements 7 are provided in areas surrounded by the light source scan lines GLA and the light source signal lines SLA. Each of the light source scan lines GLA is coupled to the peripheral circuits GC. The light source signal lines SLA and the peripheral circuits GC are coupled, through the coupling terminals CN, to the light source control circuit 131 for controlling the light-emitting elements 7 and to a power supply circuit.

FIG. 6 is a plan view illustrating a plurality of light-emitting elements. Mini LEDs each having a size of approximately 100 μm to 200 μm in the plan view can be applied as the light-emitting elements 7. Alternatively, micro LEDs each having a size of approximately 3 μm to 100 μm in the plan view may be applied as the light-emitting elements 7.

As illustrated in FIG. 6, the light-emitting elements 7 include first light-emitting elements 7-R, 7-G, and 7-B and a second light-emitting element 7-IR that emit light having different wavelengths. The first light-emitting elements 7-R, 7-G, and 7-B emit the visible light L1 (first light) in red, green, and blue, respectively. The second light-emitting element 7-IR emits infrared light, more preferably, the near-infrared light L1 (second light).

The first light-emitting element 7-R is arranged adjacent to the first light-emitting element 7-G in the first direction Dx. The first light-emitting element 7-B is arranged adjacent to the first light-emitting element 7-R in the second direction Dy. The second light-emitting element 7-IR is arranged adjacent to the first light-emitting element 7-G in the second direction Dy. The first light-emitting element 7-B is arranged adjacent to the second light-emitting element 7-IR in the first direction Dx.

Light-emitting element groups each including a group of the first light-emitting elements 7-R, 7-G, and 7-B and the second light-emitting element 7-IR are arranged in the first direction Dx and the second direction Dy. The arrangement of the first light-emitting elements 7-R, 7-G, and 7-B and the second light-emitting element 7-IR is not limited to the example illustrated in FIG. 6. Some of the first light-emitting elements 7-R, 7-G, and 7-B and the second light-emitting element 7-IR may be replaced with one another. The first light-emitting elements 7-R, 7-G, and 7-B and the second light-emitting element 7-IR may be arranged in the first direction Dx. The first light-emitting elements 7 are not limited to the first light-emitting elements 7-R, 7-G, and 7-B of three colors, and may include light-emitting elements that emit light in four or more colors including white light.

In the lighting device 3, when the display panel 2 performs the display, the first light-emitting elements 7-R, 7-G, and 7-B among the light-emitting elements 7 emit the light L1, and when the optical sensor 6 performs the detection, the first light-emitting elements 7-R, 7-G, and 7-B and the second light-emitting element 7-IR emit the light L1. During the detection, the first light-emitting elements 7-R, 7-G, and 7-B and the second light-emitting element 7-IR can emit the light L1 having different wavelengths depending on the biological information to be detected by the optical sensor 6, such as asperities (fingerprint), the blood vessel image, a pulse wave, pulsation, or a blood oxygen level of the finger Fg or a palm. For example, the first light-emitting elements 7-R, 7-G, and 7-B may emit the visible light during the fingerprint detection, and the second light-emitting element 7-IR may emit the infrared light during the detection of the blood vessel image (vein pattern).

Figure 7:
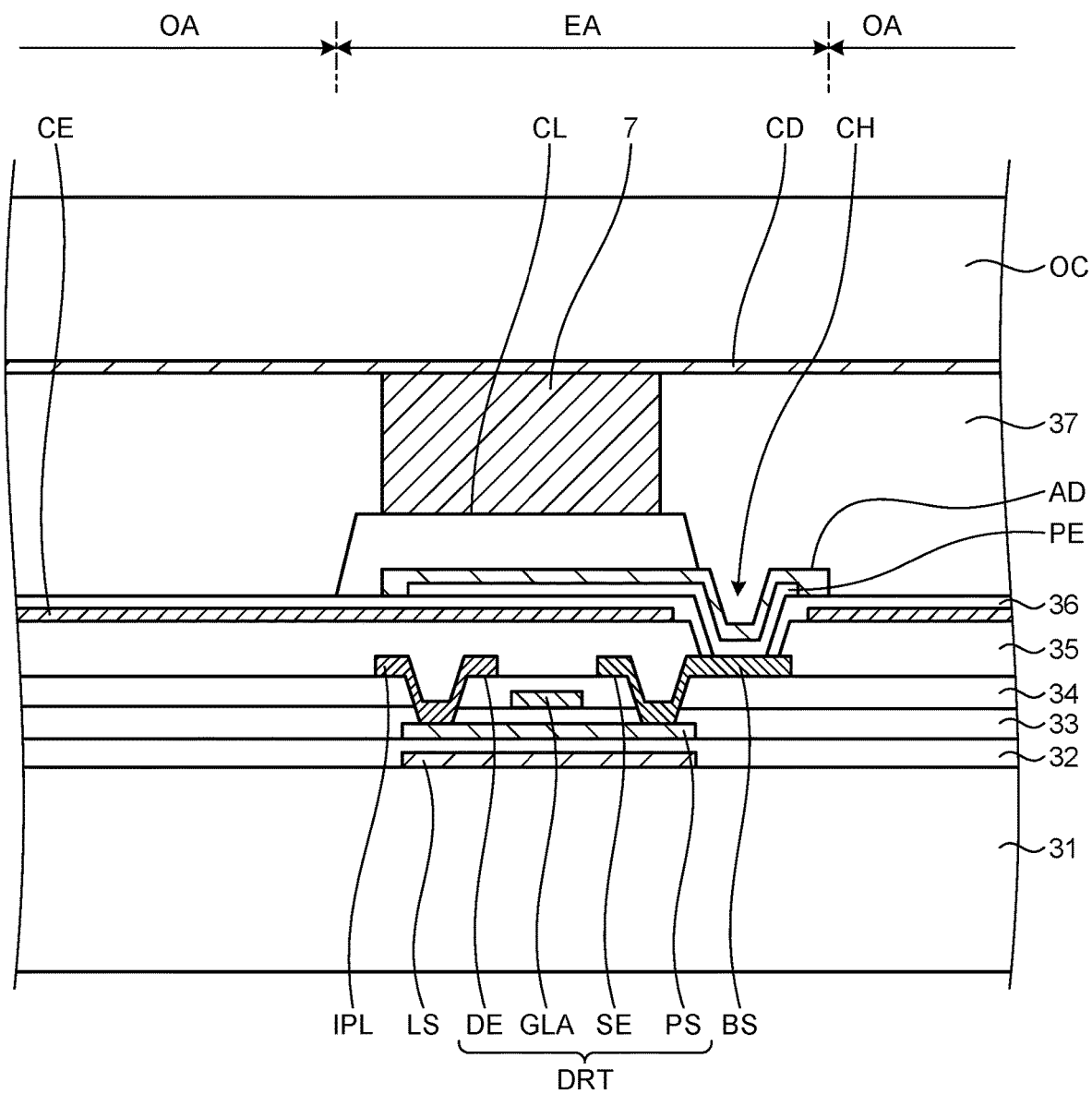
FIG. 7 is a sectional view of each of the light-emitting elements.

FIG. 7 is a sectional view of the light-emitting element. FIG. 7 also illustrates a sectional configuration of a drive transistor DRT. As illustrated in FIG. 7, the light-emitting element 7 and the drive transistor DRT are provided above the light source base member 31. The drive transistor DRT includes a semiconductor layer PS, the light source scan line GLA, a drain electrode DE, and a source electrode SE. A light-blocking layer LS, an insulating layer 32, the semiconductor layer PS, an insulating layer 33, the light source scan line GLA, an insulating layer 34, a base BS (source electrode SE) and an anode power supply line IPL (drain electrode DE), and a first organic insulating layer 35 are provided on one surface of the light source base member 31 in the order as listed. For example, a silicon oxide (SiO) film, a silicon nitride (SiN) film, or a silicon oxynitride (SiON) film is used as inorganic insulating layers such as the insulating layers 32, 33, 34, and 36. Each of the inorganic insulating layers is not limited to a single layer, and may be a multilayered film.

The light-blocking layer LS is formed of a material having lower light transmittance than that of the light source base member 31 and is provided below the semiconductor layer PS. The insulating layer 32 is provided upon the light source base member 31 so as to cover the light-blocking layer LS. The semiconductor layer PS is provided above the insulating layer 32. For example, polysilicon or an oxide semiconductor is used as the semiconductor layer PS.

The insulating layer 33 is provided above the insulating layer 32 so as to cover the semiconductor layer PS. The light source scan line GLA is provided upon the insulating layer 33. A portion of the light source scan line GLA overlapping the semiconductor layer PS serves as a gate electrode. The drive transistor DRT has a top-gate structure in which the light source scan line GLA is provided above the semiconductor layer PS. However, the drive transistor DRT is not limited thereto and may have a bottom-gate structure or a dual-gate structure.

The insulating layer 34 is provided upon the insulating layer 33 so as to cover the light source scan line GLA. The source electrode SE (base BS) and the drain electrode DE (anode power supply line IPL) are provided upon the insulating layer 34. A portion of the anode power supply line IPL overlapping the semiconductor layer PS serves as the drain electrode DE of the drive transistor DRT. A portion of the base BS overlapping the semiconductor layer PS serves as the source electrode SE of the drive transistor DRT. The source electrode SE and the drain electrode DE are coupled to the semiconductor layer PS through contact holes provided in the insulating layers 33 and 34.

The first organic insulating layer 35 is provided upon the insulating layer 34 so as to cover the anode power supply line IPL and the base BS. A light source common electrode CE, an overlapping electrode PE, and a cathode electrode CD are of indium tin oxide (ITO). An insulating layer 36 is provided between the light source common electrode CE and the overlapping electrode PE in a direction normal to the light source base member 31.

An anode electrode AD is a layered body of, for example, ITO, silver (Ag), and ITO. The anode electrode AD is provided upon the overlapping electrode PE and is coupled to the base BS through a contact hole CH provided in the first organic insulating layer 35. A coupling layer CL is formed of silver paste and is provided upon the anode electrode AD between the light source base member 31 and the light-emitting element 7. The light-emitting element 7 is provided upon the coupling layer CL and is electrically coupled to the coupling layer CL. That is, the light-emitting element 7 is electrically coupled to the anode electrode AD through the coupling layer CL.

A second organic insulating layer 37 is provided upon the insulating layer 36 so as to cover side surfaces of the light-emitting element 7. The cathode electrode CD is provided upon the second organic insulating layer 37 and the light-emitting element 7 and is electrically coupled to a cathode terminal ELED2 of the light-emitting element 7 (refer to FIG. 8). The cathode electrode CD is electrically coupled to the cathode terminals ELED2 of the light-emitting elements 7. An overcoat layer OC is provided upon the cathode electrode CD.

In the lighting device 3, an area overlapping the light-emitting element 7, the coupling layer CL, and the anode electrode AD serves as a light-emitting area EA for emitting the light L1. An area between the light-emitting elements 7 serves as an opening area OA. In other words, the opening area OA is an area not overlapping the light-emitting element 7, the coupling layer CL, the anode electrode AD, and various types of wiring such as the light source scan line GLA. The light L2 reflected by the finger Fg (refer to FIG. 1) passes through the opening area OA and travels toward the wavelength selection filter 4, the optical element 5, and the optical sensor 6.

Figure 8:
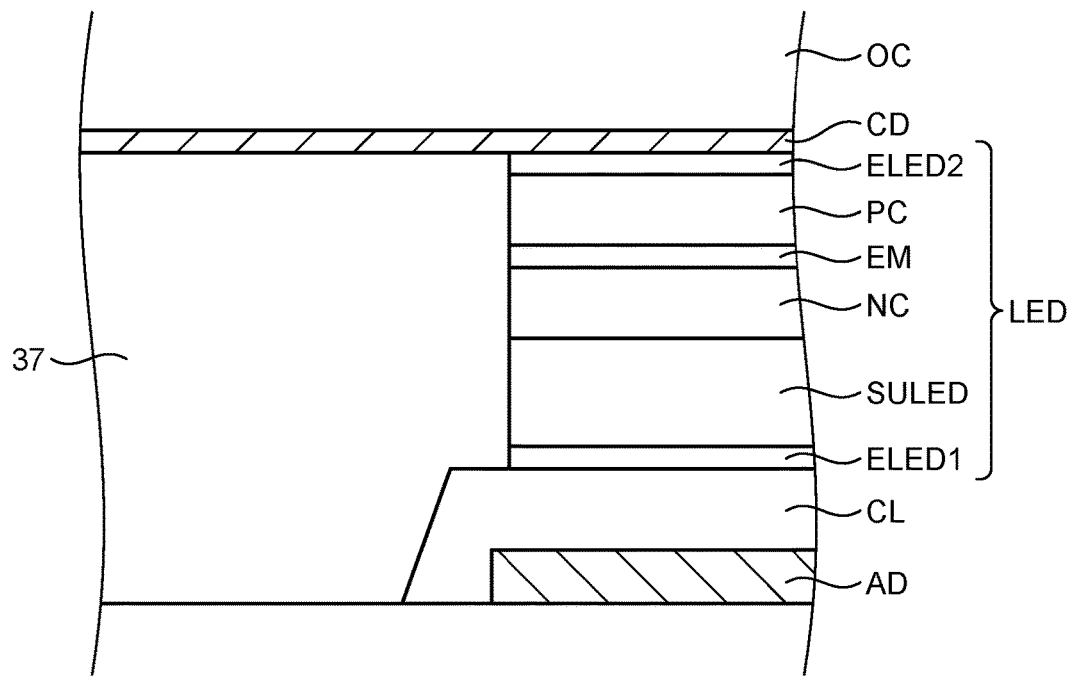
FIG. 8 is a sectional view illustrating the light-emitting element of FIG. 7 in an enlarged manner.

FIG. 8 is a sectional view illustrating the light-emitting element of FIG. 7 in an enlarged manner. As illustrated in FIG. 8, the light-emitting element 7 includes a light-emitting element substrate SULED, an n-type cladding layer NC, a light-emitting layer EM, a p-type cladding layer PC, an anode terminal ELED1, and the cathode terminal ELED2. The n-type cladding layer NC, the light-emitting layer EM, the p-type cladding layer PC, and the cathode terminal ELED2 are stacked on the light-emitting element substrate SULED in the order as listed. The anode terminal ELED1 is provided between the light-emitting element substrate SULED and the coupling layer CL.

The light-emitting layer EM is of, for example, indium gallium nitride (InGaN). The p-type cladding layer PC and the n-type cladding layer NC are of, for example, gallium nitride (GaN). The light-emitting element substrate SULED is of silicon carbide (SiC). Both the anode terminal ELED1 and the cathode terminal ELED2 are of aluminum. Each of the materials of the light-emitting layer EM, the p-type clad layer PC, and the n-type clad layer NC is merely an example and may differ between the first light-emitting elements 7-R, 7-G, and 7-B and a second light-emitting element 7-IR that emit the light having different wavelengths.

In a manufacturing process of the light-emitting element 7, manufacturing equipment forms films of the n-type cladding layer NC, the light-emitting layer EM, the p-type cladding layer PC, and the cathode terminal ELED2 upon the light-emitting element substrate SULED. Then, the manufacturing equipment forms the light-emitting element substrate SULED into a thin film, and forms the anode terminal ELED1 on the bottom surface of the light-emitting element substrate SULED. The manufacturing equipment then cuts the light-emitting element 7 into a square shape and disposes it upon the coupling layer CL.

With such a configuration, the anode (anode terminal ELED1) of the light-emitting element 7 is coupled to the anode power supply line IPL through the drive transistor DRT. The anode power supply line IPL is supplied with an anode power supply potential PVDD. The cathode (cathode terminal ELED2) of the light-emitting element 7 is supplied with a cathode reference potential. The anode power supply potential PVDD is a higher potential than the cathode reference potential. As a result, the light-emitting element 7 is supplied with a forward current (drive current) by a potential difference between the anode power supply potential PVDD and the cathode reference potential, and thereby, emits light. The configuration of the light-emitting element 7 illustrated in FIGS. 7 and 8 is merely an example. The light-emitting element having another configuration may be employed.

Figure 9:
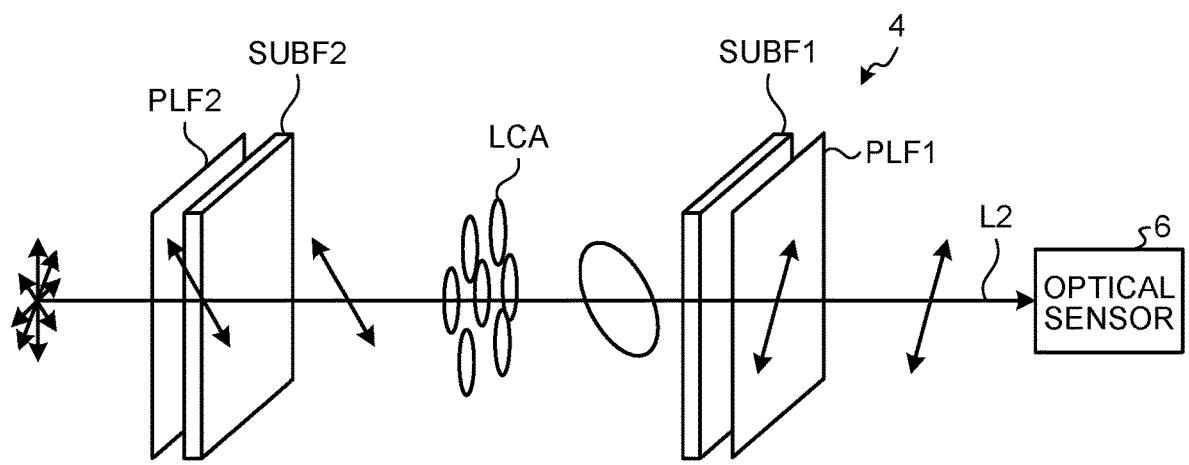
FIG. 9 is an explanatory diagram for explaining a polarization state of light passing through a wavelength selection filter.

FIG. 9 is an explanatory diagram for explaining a polarization state of the light passing through the wavelength selection filter. The configuration of the wavelength selection filter 4 is the same as that of the display panel 2 illustrated in FIG. 3 and will not be described in detail. However, the wavelength selection filter 4 may not include the color filter CF illustrated in FIG. 3. In addition, the arrangement pitch of pixel electrodes of the wavelength selection filter 4 is greater than the arrangement pitch of the sub-pixels SPX.

As illustrated in FIG. 9, the first polarization axis of the first polarizing plate PLF1 and the second polarization axis of the second polarizing plate PLF2 are in a positional relation of, for example, crossed Nicols. The light L2 reflected by the finger Fg is converted into linearly polarized light parallel to the second polarization axis of the second polarizing plate PLF2 by the second polarizing plate PLF2 and is incident on the liquid crystal layer LCA. The light L2 passes through the liquid crystal layer LCA to be converted into elliptically polarized light corresponding to the phase difference δ of the liquid crystal layer LCA. Then, a component parallel to the first polarization axis of the first polarizing plate PLF1 passes through the wavelength selection filter 4 and is incident on the optical sensor 6.

A light intensity T of the light L2 that passes through the wavelength selection filter 4 is represented as Expression (1) below. The phase difference δ of the liquid crystal layer LCA is represented as Expression (2) below. In Expression (2), Δn denotes the birefringence index of the liquid crystal layer LCA, and d denotes the thickness of the liquid crystal layer LCA. The phase difference δ of the liquid crystal layer LCA is inversely proportional to a wavelength λ. The birefringence index Δn continuously changes with a voltage applied to the liquid crystal layer LCA. That is, the light intensity T can be controlled by applying the voltage to the liquid crystal layer LCA. As a result, the wavelength selection filter 4 can vary the transmission band for transmitting the light L2 and the non-transmission band for not transmitting the light L2.

$$T=\sin(\delta/2)^2 \quad (1)$$

$$\delta=(2\pi/\lambda)\times\Delta n\times d \quad (2)$$

Figure 10:
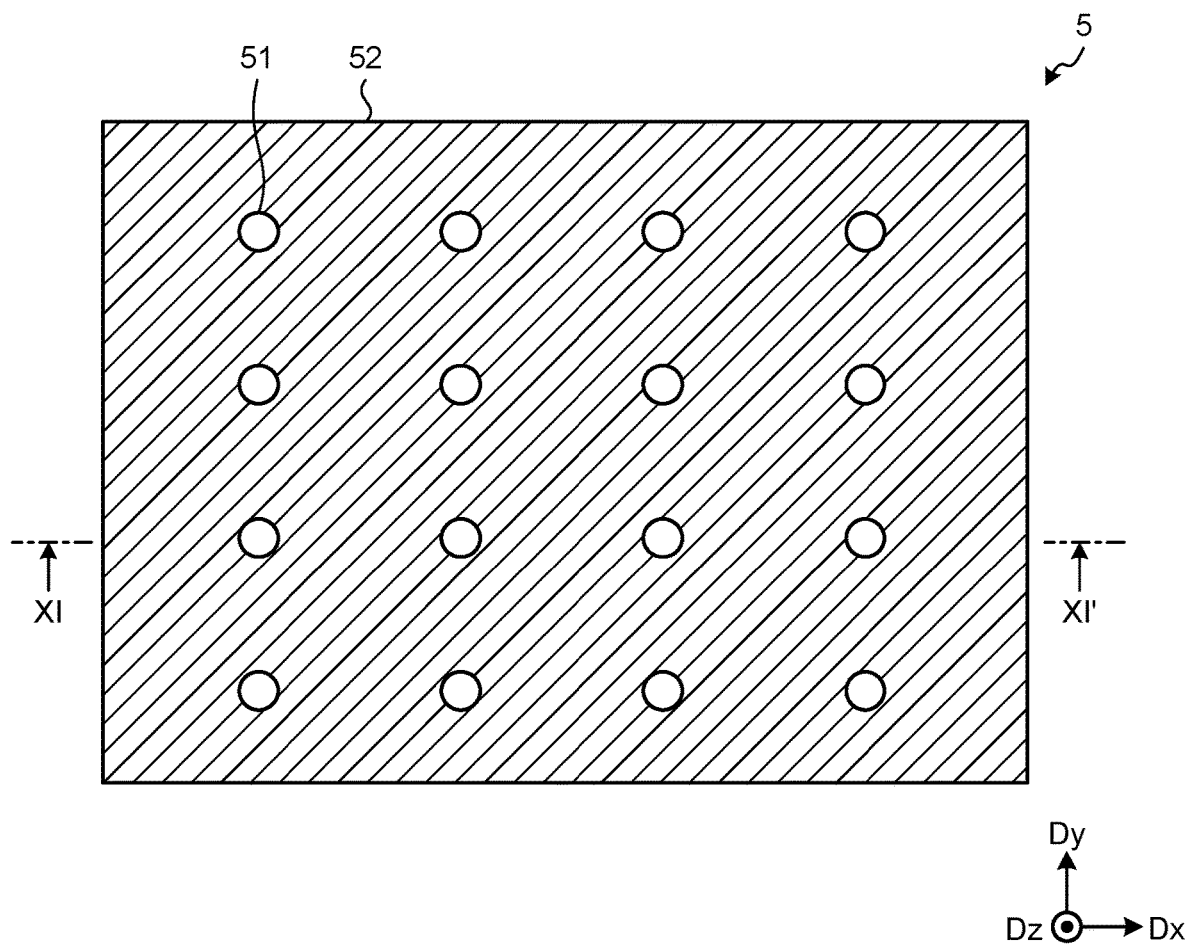
FIG. 10 is a plan view illustrating an optical element.
Figure 11:
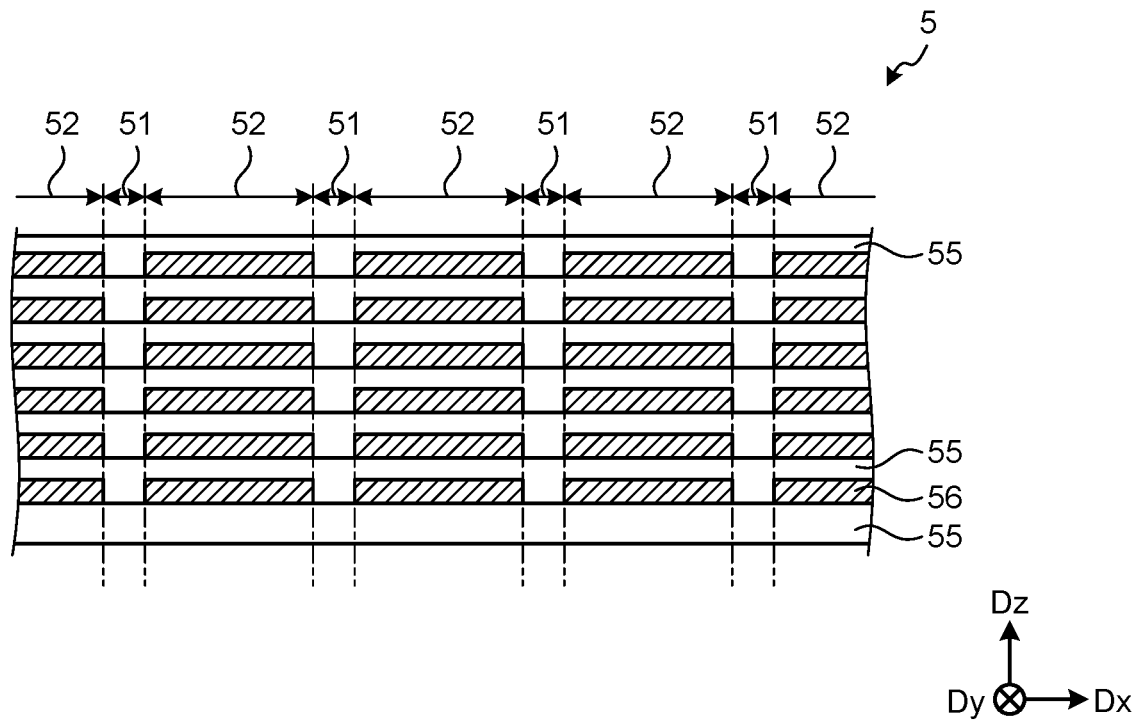
FIG. 11 is a XI-XI' sectional view of FIG. 10.

FIG. 10 is a plan view illustrating the optical element. FIG. 11 is a XI-XI' sectional view of FIG. 10. The optical element 5 includes the light-transmitting areas 51 and the non-light-transmitting area 52. Each of the light-transmitting areas 51 is provided in a position overlapping the photoelectric conversion element 8. The light-transmitting areas 51 are arranged in the first direction Dx and the second direction Dy in the plan view. The non-light-transmitting area 52 is an area between the light-transmitting areas 51. The light-transmitting area 51 is circular in the plan view. However, the shape in the plan view of the light-transmitting area 51 may be changed as appropriate depending on the shape of a light-receiving surface of the photoelectric conversion element 8. The light-transmitting area 51 is not limited to being circular, and may be, for example, quadrilateral, polygonal, elliptical, or irregular-shaped.

As illustrated in FIG. 11, the optical element 5 includes a light-transmitting resin 55 and a non-light-transmitting resin 56. A plurality of layers of the light-transmitting resin 55 are stacked in the third direction Dz. The non-light-transmitting resin 56 is provided between the layers of the light-transmitting resin 55 in an area overlapping the non-light-transmitting area 52. The light-transmitting resin 55 is a light-transmitting resin material that transmits the visible light and the near-infrared light. The non-light-transmitting resin 56 is a material having lower light transmittance than that of the light-transmitting resin 55. The non-light-transmitting resin 56 is a colored resin material such as a black resin material.

In other words, the light-transmitting areas 51 are areas not overlapping the non-light-transmitting resin 56 and are formed of only the light-transmitting resin 55 from one surface to the other surface of the optical element 5. The non-light-transmitting area 52 is an area including at least one layer of the non-light-transmitting resin 56 between the one surface and the other surface of the optical element 5. With such a configuration, the optical element 5 can allow the light L2 to pass through the light-transmitting areas 51, and prevent the light L2 from passing through the non-light-transmitting area 52.

Figure 12:
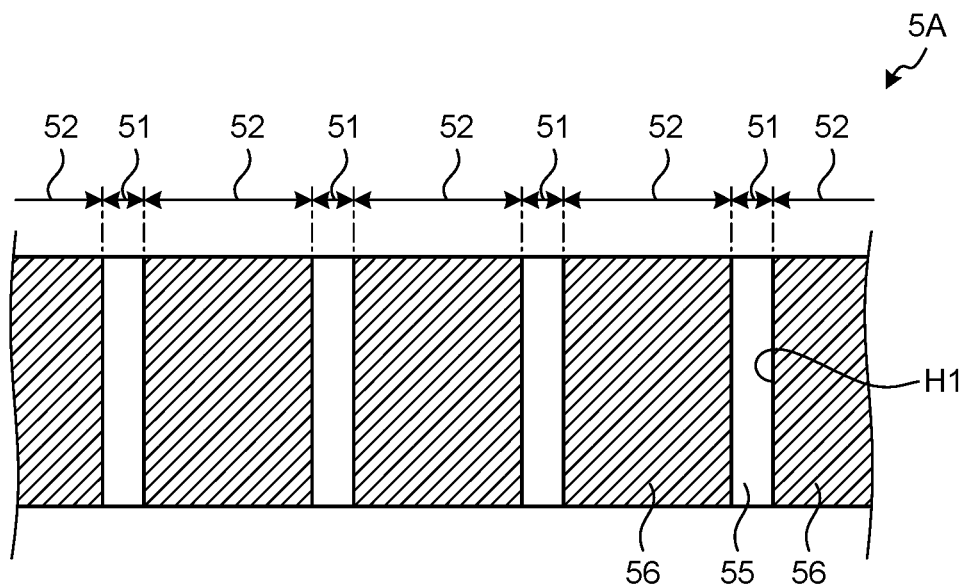
FIG. 12 is a sectional view illustrating an optical element according to a first modification.

FIG. 12 is a sectional view illustrating an optical element according to a first modification. As illustrated in FIG. 12, in an optical element 5A according to the first modification, the non-light-transmitting resin 56 is formed into a flat plate shape and is provided with through-holes H1 in areas overlapping the light-transmitting areas 51. The through-holes H1 penetrate from one surface to the other surface of the optical element 5A. The light-transmitting resin 55 is provided in the through-holes H1 and is formed into a column shape extending in the third direction Dz.

Figure 13:
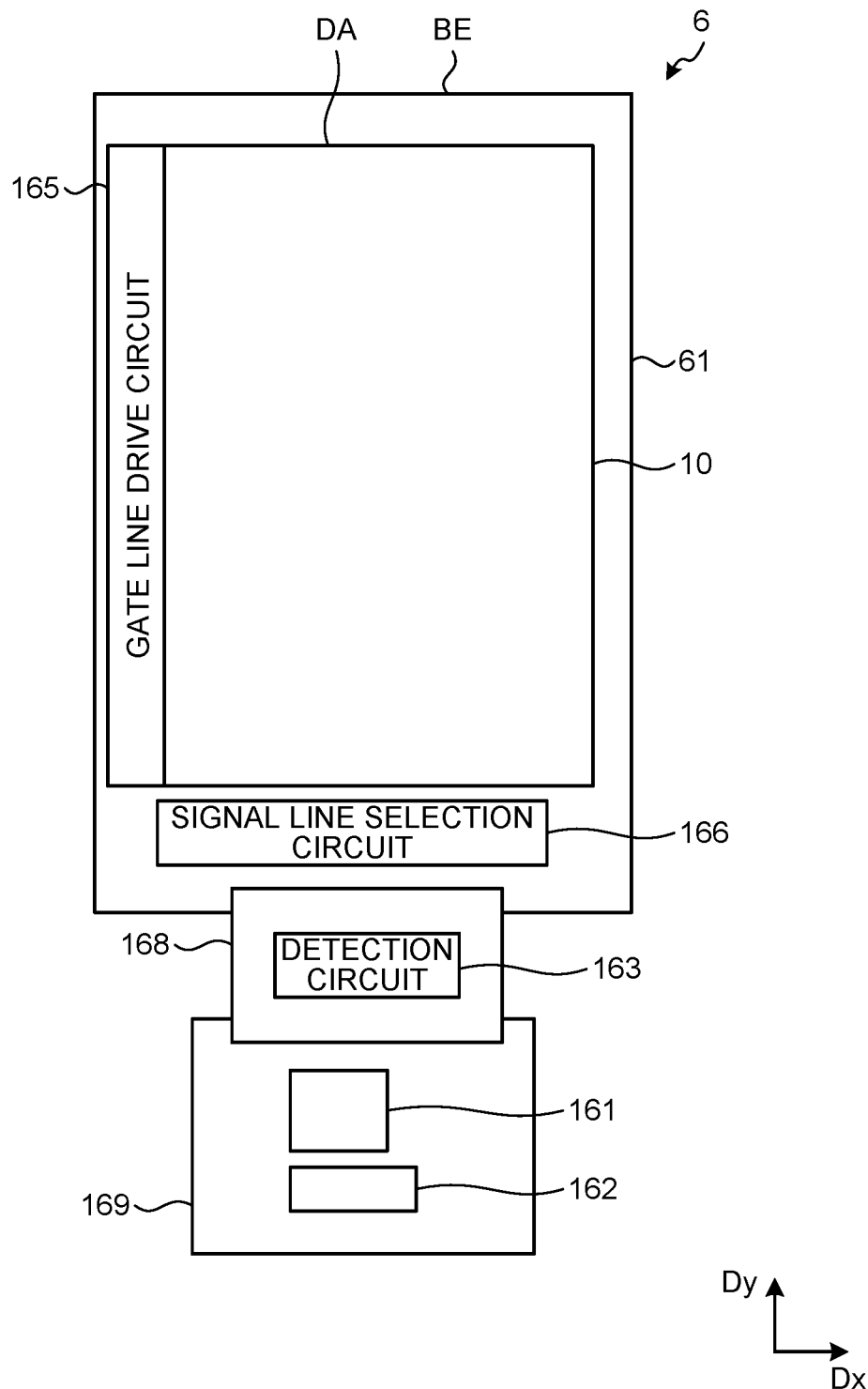
FIG. 13 is a plan view illustrating an optical sensor.

FIG. 13 is a plan view illustrating the optical sensor. As illustrated in FIG. 13, the optical sensor 6 includes the sensor base member 61, a sensor device 10, a gate line drive circuit 165, a signal line selection circuit 166, the detection control circuit 161, a power supply circuit 162, and the detection circuit 163.

A control board 169 is electrically coupled to the sensor base member 61 through a flexible printed circuit board 168. The flexible printed circuit board 168 is provided with the detection circuit 163. The control board 169 is provided with the detection control circuit 161 and the power supply circuit 162. The detection control circuit 161 is, for example, a field programmable gate array (FPGA). The detection control circuit 161 supplies control signals to the sensor device 10, the gate line drive circuit 165, and the signal line selection circuit 166 to control a detection operation of the sensor device 10. The power supply circuit 162 supplies voltage signals including, for example, a sensor power supply signal VDDSNS (refer to FIG. 15) to the sensor device 10, the gate line drive circuit 165, and the signal line selection circuit 166.

The sensor device 10 is provided in an area of the sensor base member 61 overlapping the display area DA. The sensor device 10 is provided with the photoelectric conversion elements 8. That is, the optical sensor 6 can detect the biological information on, for example, the finger Fg in the area overlapping the entire display area DA. The gate line drive circuit 165 and the signal line selection circuit 166 are provided in the peripheral area BE. Specifically, the gate line drive circuit 165 is provided in an area of the peripheral area BE extending along the second direction Dy. The signal line selection circuit 166 is provided in an area of the peripheral area BE extending along the first direction Dx between the sensor device 10 and the detection circuit 163.

The gate line drive circuit 165 is a circuit that drives a plurality of sensor scan lines GLB (refer to FIG. 14) based on the various control signals. The gate line drive circuit 165 sequentially or simultaneously selects the sensor scan lines GLB and supplies a gate drive signal Vgl to each of the selected sensor scan lines GLB. By this operation, the gate line drive circuit 165 selects the photoelectric conversion elements 8 coupled to the sensor scan lines GLB.

Figure 14:
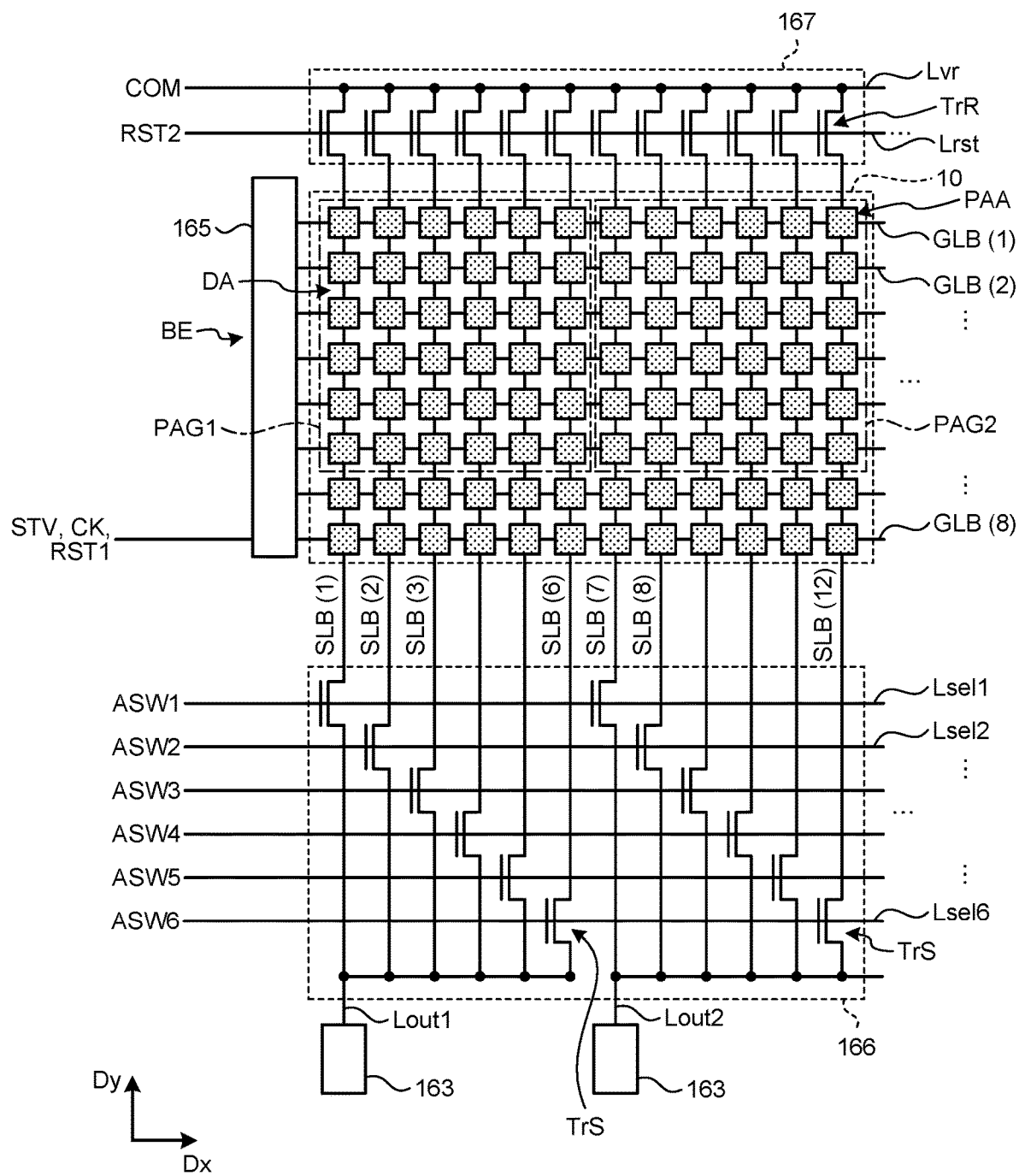
FIG. 14 is a circuit diagram illustrating the optical sensor.

The signal line selection circuit 166 is a switch circuit that sequentially or simultaneously selects a plurality of sensor signal lines SLB (refer to FIG. 14). The signal line selection circuit 166 is, for example, a multiplexer. The signal line selection circuit 166 couples the selected sensor signal lines SLB to the detection circuit 163 based on a selection signal ASW supplied from the detection control circuit 161. By this operation, the signal line selection circuit 166 outputs the detection signal Vdet of each of the photoelectric conversion elements 8 to the detection circuit 163.

The detection circuit 163 is, for example, an analog front end (AFE) circuit. The detection circuit 163 is a signal processing circuit at least having functions of a detection signal amplifier and an analog-to-digital (A/D) converter. The detection signal amplifier amplifies the detection signal Vdet. The A/D converter converts an analog signal output from the detection signal amplifier into a digital signal.

Figure 15:
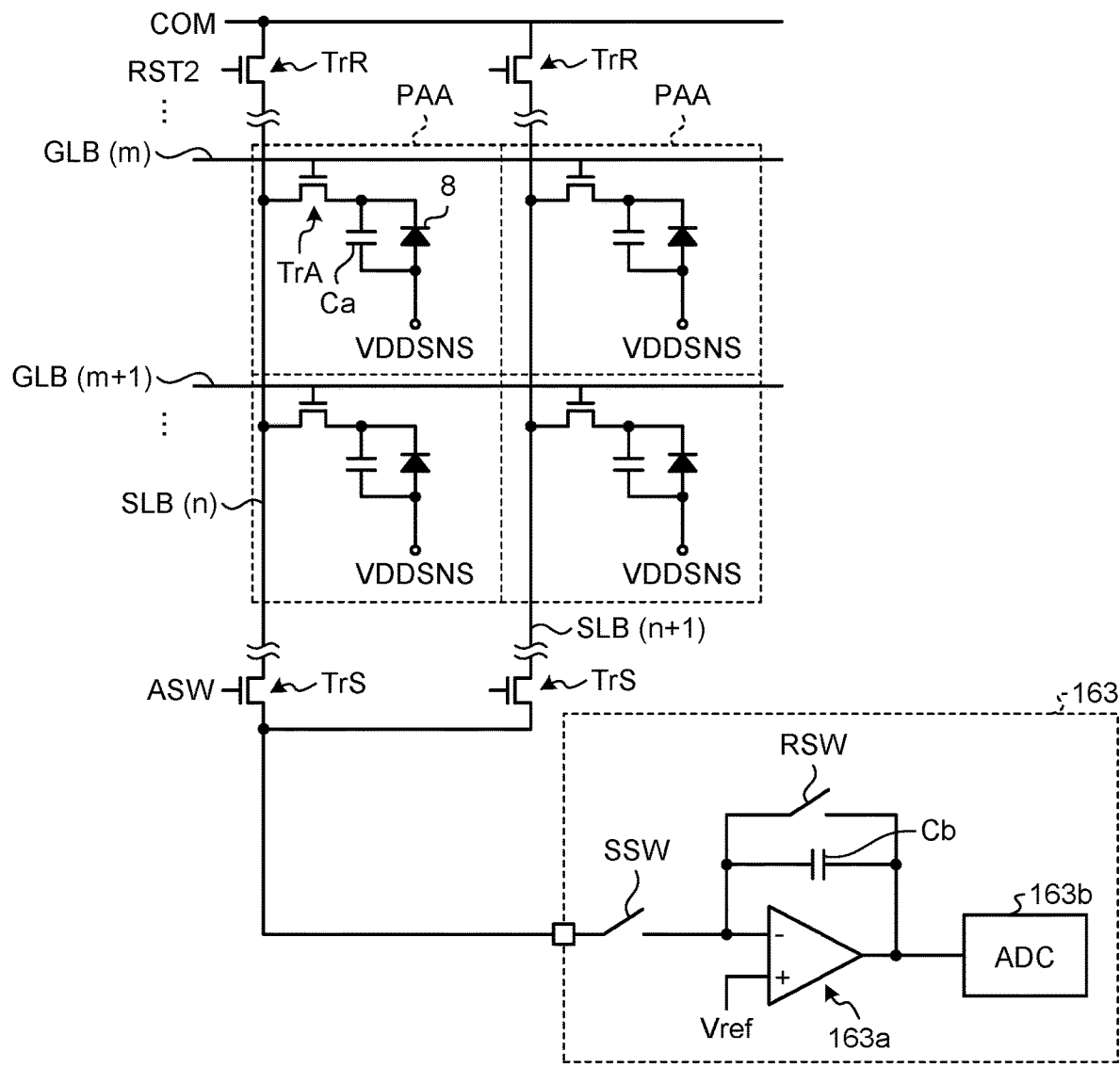
FIG. 15 is a circuit diagram illustrating a plurality of partial detection areas.

FIG. 14 is a circuit diagram illustrating the optical sensor. FIG. 15 is a circuit diagram illustrating a plurality of partial detection areas. As illustrated in FIG. 14, the sensor device 10 has a plurality of partial detection areas PAA arranged in a matrix having a row-column configuration. Each of the partial detection areas PAA is provided with the photoelectric conversion element 8.

The sensor scan lines GLB extend in the first direction Dx and are coupled to the partial detection areas PAA arranged in the first direction Dx. A plurality of sensor scan lines GLB(1), GLB(2), . . . , GLB(8) are arranged in the second direction Dy and are each coupled to the gate line drive circuit 165. In the following description, the sensor scan lines GLB(1), GLB(2), . . . , GLB(8) will each be simply referred to as the sensor scan lines GLB when they need not be distinguished from one another. For ease of understanding of the description, FIG. 14 illustrates eight of the sensor scan lines GLB. However, this is merely an example, and M (where M is eight or greater, and is, for example, 256) sensor scan lines GLB may be arranged.

The sensor signal lines SLB extend in the second direction Dy and are coupled to the photoelectric conversion elements 8 of the partial detection areas PAA arranged in the second direction Dy. A plurality of sensor signal lines SLB(1), SLB(2), . . . , SLB(12) are arranged in the first direction Dx and are each coupled to the signal line selection circuit 166 and a reset circuit 167. In the following description, the sensor signal lines SLB(1), SLB(2), . . . , SLB(12) will each be simply referred to as the sensor signal lines SLB when they need not be distinguished from one another.

For ease of understanding of the description, 12 of the sensor signal lines SLB are illustrated. However, this is merely an example, and N (where N is 12 or greater, and is, for example, 252) sensor signal lines SLB may be arranged. In FIG. 14, the sensor device 10 is provided between the signal line selection circuit 166 and the reset circuit 167. The present disclosure is not limited thereto. The signal line selection circuit 166 and the reset circuit 167 may be coupled to ends of the sensor signal lines SLB in the same direction.

The gate line drive circuit 165 receives the various control signals such as a start signal STV, a clock signal CK, and a reset signal RST1 from the detection control circuit 161 (refer to FIG. 13). The gate line drive circuit 165 sequentially selects the sensor scan lines GLB(1), GLB(2), . . . , GLB(8) in a time-division manner based on the various control signals. The gate line drive circuit 15 supplies the gate drive signal Vgl to the selected one of the sensor scan lines GLB. This operation supplies the gate drive signal Vgl to a plurality of sensor switching elements TrA coupled to the sensor scan lines GLB, and the partial detection areas PAA arranged in the first direction Dx are selected as detection targets.

The gate line drive circuit 165 may perform different driving in each of detection modes for detecting the fingerprint and for detecting the different pieces of biological information (such as the pulse wave, the pulsation, the blood vessel image, and the blood oxygen level). For example, the gate line drive circuit 165 may drive the sensor scan lines GLB collectively. The gate line drive circuit 165 may perform the driving for each area according to the wavelength of the light L2.

Specifically, the gate line drive circuit 165 simultaneously selects a predetermined number of the sensor scan lines GLB from among the sensor scan lines GLB(1), GLB(2), . . . , GLB(8) based on the control signals. For example, the gate line drive circuit 165 simultaneously selects six sensor scan lines GLB(1) to GLB(6) and supplies thereto the gate drive signals Vgl. The gate line drive circuit 165 supplies the gate drive signals Vgl through the selected six sensor scan lines GLB to the sensor switching elements TrA. By this operation, detection group areas PAG1 and PAG2 each including the partial detection areas PAA arranged in the first direction Dx and the second direction Dy are selected as the detection targets. The gate line drive circuit 165 collectively drives the predetermined number of the sensor scan lines GLB and sequentially supplies the gate drive signals Vgl to the sensor scan lines GLB in units of the predetermined number of the sensor scan lines GLB.

The signal line selection circuit 166 includes a plurality of selection signal lines Lsel, a plurality of output signal lines Lout, and signal line switching elements TrS. The signal line switching elements TrS are provided corresponding to the sensor signal lines SLB. Six sensor signal lines SLB(1), SLB(2), . . . , SLB(6) are coupled to a common output signal line Lout1. Six sensor signal lines SLB(7), SLB(8), . . . , SLB(12) are coupled to a common output signal line Lout2. The output signal lines Lout1 and Lout2 are each coupled to the detection circuit 163.

The sensor signal lines SLB(1), SLB (2), . . . , SLB(6) are grouped into a first signal line block, and the sensor signal lines SLB(7), SLB(8), . . . , SLB(12) are grouped into a second signal line block. The selection signal lines Lsel are respectively coupled to the gates of the signal line switching elements TrS included in one signal line block. One selection signal line Lsel is coupled to the gate of the signal line switching element TrS in each of the signal line blocks.

Specifically, selection signal lines Lsel1, Lsel2, . . . , Lsel6 are coupled to the signal line switching elements TrS corresponding to the sensor signal lines SLB(1), SLB (2), . . . , SLB(6), respectively. The selection signal line Lsel1 is coupled to the signal line switching element TrS corresponding to the sensor signal line SLB(1) and the signal line switching element TrS corresponding to the sensor signal line SLB(7). The selection signal line Lsel2 is coupled to the signal line switching element TrS corresponding to the sensor signal line SLB(2) and the signal line switching element TrS corresponding to the sensor signal line SLB(8).

The detection control circuit 161 (refer to FIG. 13) sequentially supplies the selection signal ASW to the selection signal lines Lsel. By the operations of the signal line switching elements TrS, the signal line selection circuit 166 sequentially selects the sensor signal lines SLB in one signal line block in a time-division manner. The signal line selection circuit 166 selects one of the sensor signal lines SLB in each of the signal line blocks. With the above-described configuration, the optical sensor 6 can reduce the number of integrated circuits (ICs) including the detection circuit 163 or the number of terminals of the ICs.

The signal line selection circuit 166 may collectively couple the sensor signal lines SLB to the detection circuit 163. Specifically, the detection control circuit 161 simultaneously supplies the selection signals ASW to the selection signal lines Lsel. As a result, the signal line selection circuit 166 operates the signal line switching elements TrS to select the sensor signal lines SLB (for example, six signal lines SGL) in one of the signal line blocks and couples the sensor signal lines SLB to the detection circuit 163. As a result, signals detected in the detection group areas PAG1 and PAG2 are output to the detection circuit 163. In this case, signals from the partial detection areas PAA (photodiodes PD) included in each of the detection group areas PAG1 and PAG2 are integrated to be output to the detection circuit 163.

By the operations of the gate line drive circuit 165 and the signal line selection circuit 166, the detection is performed for each of the detection group areas PAG1 and PAG2. As a result, the intensity of the detection signal Vdet obtained by one time of detection increases, so that the sensor sensitivity can be improved. In addition, time required for the detection can be reduced. Consequently, the optical sensor 6 can repeatedly perform the detection in a short time, and thus, can improve a signal-to-noise (S/N) ratio, and can accurately detect a change in the biological information with time, such as the pulse wave.

As illustrated in FIG. 14, the reset circuit 167 includes a reference signal line Lvr, a reset signal line Lrst, and reset switching elements TrR. The reset switching elements TrR are provided corresponding to the sensor signal lines SLB. The reference signal line Lvr is coupled to either the sources or the drains of the reset switching elements TrR. The reset signal line Lrst is coupled to the gates of the reset switching elements TrR.

The detection control circuit 161 supplies a reset signal RST2 to the reset signal line Lrst. This operation turns on the reset switching elements TrR to electrically couple the sensor signal lines SLB to the reference signal line Lvr. The power supply circuit 162 supplies a reference signal COM to the reference signal line Lvr. This operation supplies the reference signal COM to a capacitive element Ca (refer to FIG. 15) included in each of the partial detection areas PAA.

As illustrated in FIG. 15, each of the partial detection areas PAA includes the photoelectric conversion element 8, the capacitive element Ca, and the sensor switching element TrA. FIG. 15 illustrates two sensor scan lines GLB(m) and GLB(m+1) arranged in the second direction Dy among the sensor scan lines GLB, and illustrates two sensor signal lines SLB(n) and SLB(n+1) arranged in the first direction Dx among the sensor signal lines SLB. The partial detection area PAA is an area surrounded by the sensor scan lines GLB and the sensor signal lines SLB. The sensor switching elements TrA are provided corresponding to the photoelectric conversion elements 8. The sensor switching element TrA includes a thin-film transistor, and in this example, includes an n-channel MOSTFT.

The gates of the sensor switching elements TrA belonging to the partial detection areas PAA arranged in the first direction Dx are coupled to the sensor scan line GLB. The sources of the sensor switching elements TrA belonging to the partial detection areas PAA arranged in the second direction Dy are coupled to the sensor signal line SLB. The drain of the sensor switching element TrA is coupled to the cathode of the photoelectric conversion element 8 and the capacitive element Ca.

The anode of the photoelectric conversion element 8 is supplied with the sensor power supply signal VDDSNS from the power supply circuit 162. The sensor signal line SLB and the capacitive element Ca are supplied with the reference signal COM as an initial potential of the sensor signal line SLB and the capacitive element Ca from the power supply circuit 162.

When the partial detection area PAA is irradiated with the light L2, a current corresponding to a light amount flows through the photoelectric conversion element 8. As a result, an electrical charge is stored in the capacitive element Ca. After the sensor switching element TrA is turned on, a current corresponding to the electrical charge stored in the capacitive element Ca flows through the sensor signal line SLB. The sensor signal line SLB is coupled to the detection circuit 163 through a corresponding one of the signal line switching elements TrS of the signal line selection circuit 166. Thus, the optical sensor 6 can detect a signal corresponding to the light amount of the light emitted to the photoelectric conversion element 8 in each of the partial detection areas PAA or a signal corresponding to the light amounts of the light emitted to the photoelectric conversion elements 8 in each detection group areas PAG1 and PAG2.

A switch SSW of the detection circuit 163 is turned on during a reading period Pdet (refer to FIG. 18), whereby the detection circuit 163 is coupled to the sensor signal lines SLB. A detection signal amplifier 163a of the detection circuit 163 converts a variation of a current supplied from the sensor signal line SLB into a variation of a voltage and amplifies the result. A reference voltage (Vref) having a fixed potential is supplied to a non-inverting input portion (+) of the detection signal amplifier 163a, and the sensor signal lines SLB are coupled to an inverting input portion (−) of the detection signal amplifier 163a. In the present embodiment, the same signal as the reference signal COM is supplied as the reference voltage (Vref). The detection signal amplifier 163a includes a capacitive element Cb and a reset switch RSW. The reset switch RSW is turned on during a reset period Prst (refer to FIG. 18), whereby an electrical charge of the capacitive element Cb is reset.

Figure 16:
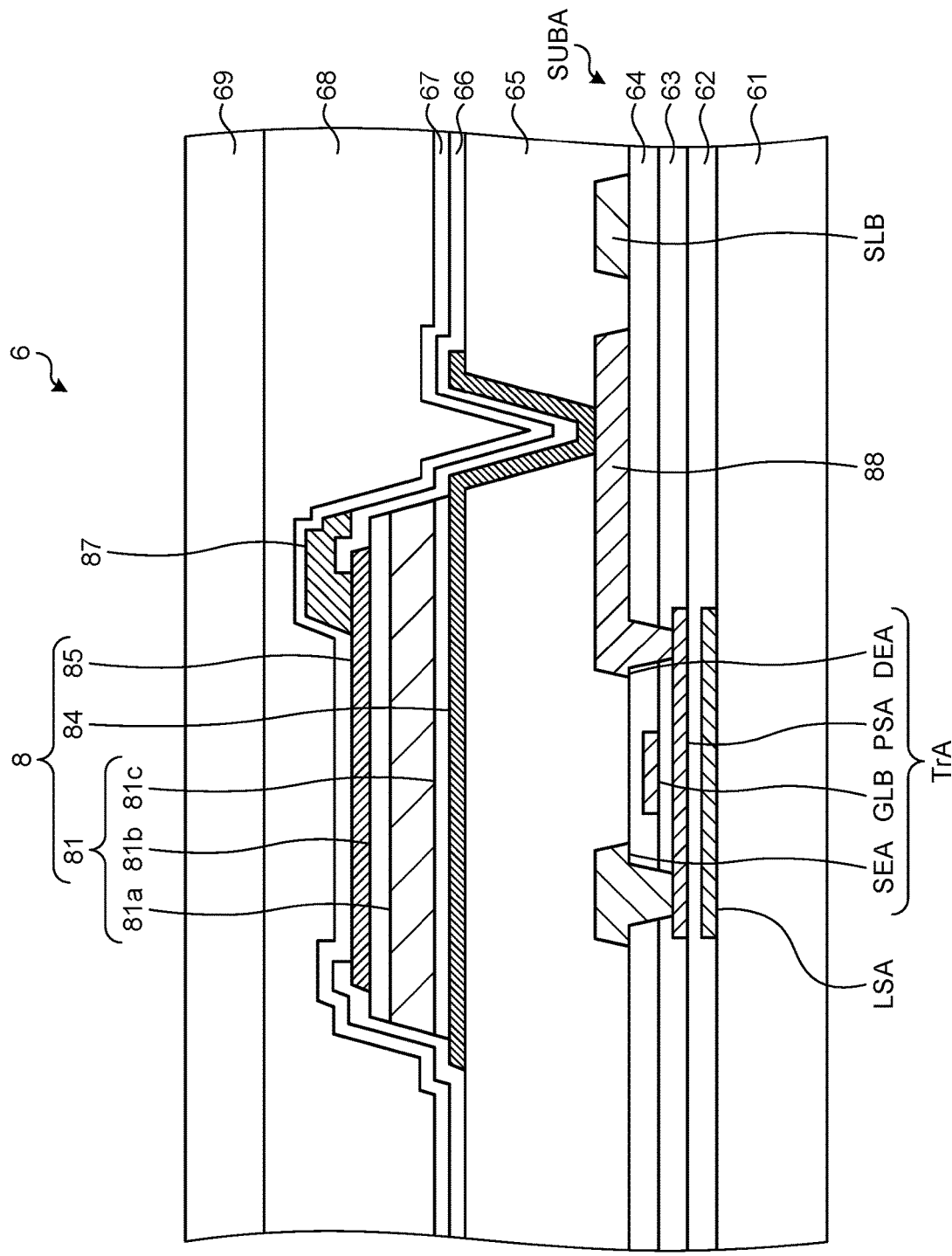
FIG. 16 is a sectional view illustrating a schematic sectional configuration of a photoelectric conversion element.

The following describes a configuration of the photoelectric conversion element 8. FIG. 16 is a sectional view illustrating a schematic sectional configuration of the photoelectric conversion element. FIG. 16 also illustrates a sectional configuration of the sensor switching element TrA. As illustrated in FIG. 16, in the photoelectric conversion element 8, a lower electrode 84, a semiconductor 81, and an upper electrode 85 are stacked upon a first organic insulating layer 65 of a sensor array substrate SUBA in the order as listed. That is, the lower electrode 84 faces the upper electrode 85 with the semiconductor 81 serving as a photoelectric conversion layer interposed therebetween in a direction orthogonal to the surface of the sensor base member 61. The sensor array substrate SUBA is a drive circuit substrate for driving a sensor for each predetermined detection area. The sensor array substrate SUBA includes, for example, the sensor base member 61, the sensor switching element TrA, and various types of wiring.

The photoelectric conversion element 8 is a positive-intrinsic-negative (PIN) photodiode. The semiconductor 81 is of amorphous silicon (a-Si). The semiconductor 81 includes an i-type semiconductor 81a, a p-type semiconductor 81b, and an n-type semiconductor 81c. The i-type semiconductor 81a, the p-type semiconductor 81b, and the n-type semiconductor 81c are a specific example of the photoelectric conversion element. In FIG. 16, the n-type semiconductor 81c, the i-type semiconductor 81a, and the p-type semiconductor 81b are stacked in the direction orthogonal the surface of the sensor base member 61 in the order as listed. However, a reversed configuration may be employed. That is, the p-type semiconductor 81b, the i-type semiconductor 81a, and the n-type semiconductor 81c may be stacked in the order as listed.

The lower electrode 84 is the cathode of the photoelectric conversion element 8 and is an electrode for reading the detection signal. The upper electrode 85 is the anode of the photoelectric conversion element 8 and is an electrode for supplying the sensor power supply signal VDDSNS to the photoelectric conversion element 8.

An insulating layer 66 and an insulating layer 67 are provided upon the first organic insulating layer 65. The insulating layer 66 covers a peripheral portion of the upper electrode 85 and is provided with an opening in a position overlapping the upper electrode 85. Coupling wiring 87 is coupled to the upper electrode 85 at a portion of the upper electrode 85 not provided with the insulating layer 66. The coupling wiring 87 is wiring for coupling the upper electrode 85 to a power supply signal line Lvs. The insulating layer 67 is provided upon the insulating layer 66 so as to cover the upper electrode 85 and the coupling wiring 87. A second organic insulating layer 68 serving as a planarizing layer and an overcoat layer 69 are provided upon the insulating layer 67.

As illustrated in FIG. 16, the sensor switching element TrA is provided on the sensor base member 61. Specifically, a light-blocking layer LSA, an insulating layer 62, a semiconductor layer PSA, an insulating layer 63, each of the sensor scan lines GLB, an insulating layer 64, a source electrode SEA and a coupling line 88 (drain electrode DEA), and the first organic insulating layer 65 are provided on one surface of the sensor base member 61 in the order as listed. For example, a silicon oxide (SiO) film, a silicon nitride (SiN) film, or a silicon oxynitride (SiON) film is used as inorganic insulating layers such as the insulating layers 62, 63, 64, 66, and 67. Each of the inorganic insulating layers is not limited to a single layer and may be a multilayered film. The lower electrode 84 of the photoelectric conversion element 8 is coupled to the coupling line 88 through a contact hole provided in the first organic insulating layer 65. The sensor switching element TrA is similar to the above-described drive transistor DRT (refer to FIG. 7), and therefore, will not be described in detail.

Although an amorphous silicon material is used as the photoelectric conversion element 8, an organic material, for example, may instead be used. Polysilicon may be used to form a PIN photodiode as the photoelectric conversion element 8.

Figure 17:
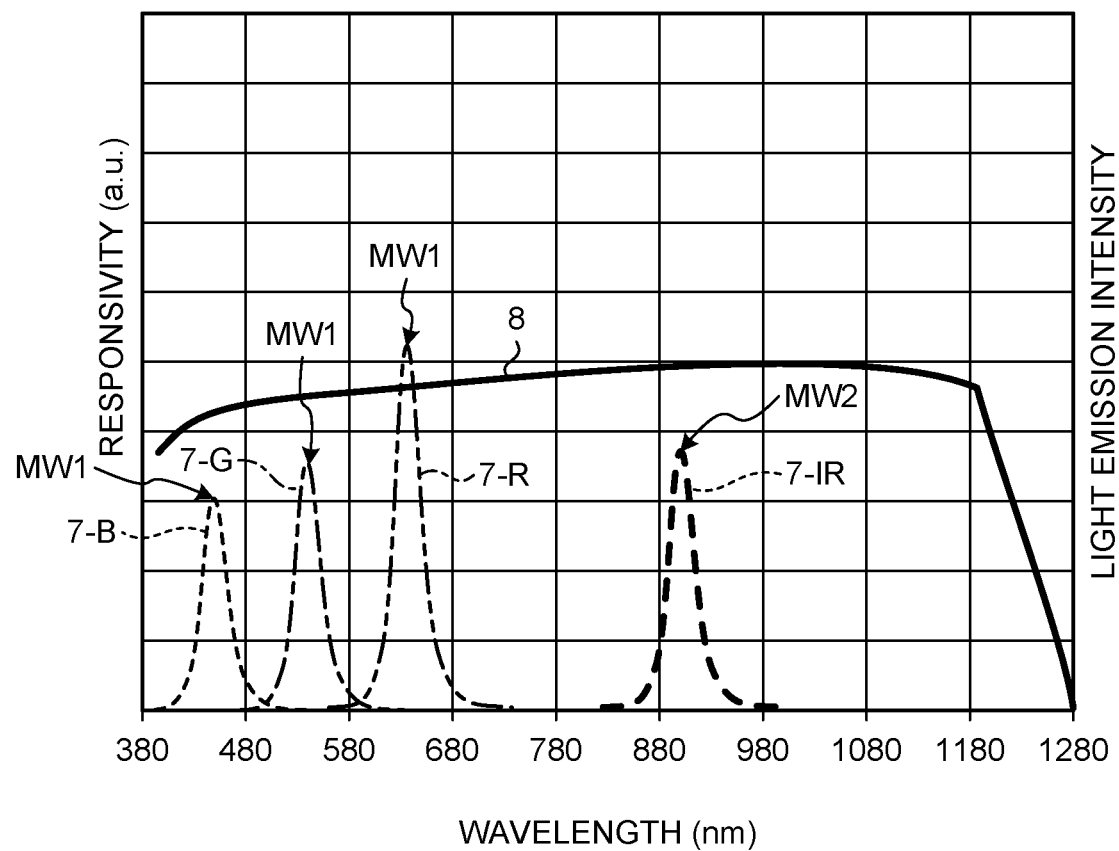
FIG. 17 is a graph illustrating relations of responsivity of the photoelectric conversion element and a light emission intensity of the light-emitting elements with a wavelength.

FIG. 17 is a graph illustrating relations of responsivity of the photoelectric conversion element and a light emission intensity of the light-emitting elements with the wavelength. In the graph illustrated in FIG. 17, the horizontal axis represents the wavelength, and the vertical axis represents the responsivity of the photoelectric conversion element 8 and the light emission intensity of the light-emitting element 7. As illustrated in FIG. 17, the first light-emitting elements 7-R, 7-G, and 7-B and the second light-emitting element 7-IR have different maximum emission wavelengths from one another. The term "maximum emission wavelength" refers to a wavelength that exhibits the maximum emission intensity in an emission spectrum representing a relation between the wavelength and the emission intensity of each beam of the light L1 emitted from the light-emitting element 7.

The first light-emitting element 7-R has a first maximum emission wavelength MW1 from 580 nm to 700 nm, for example, at approximately 660 nm. The first light-emitting element 7-G has another first maximum emission wavelength MW1 from 500 nm to 600 nm, for example, at approximately 560 nm. The first light-emitting element 7-B has still another first maximum emission wavelength MW1 from 420 nm to 520 nm, for example, at approximately 470 nm. The second light-emitting element 7-IR has a second maximum emission wavelength MW2 from 850 nm to 950 nm, for example, at approximately 900 nm.

The photoelectric conversion element 8 has the responsivity in a region ranging from a visible light region to a near-infrared region. That is, the photoelectric conversion element 8 has the responsivity in a wavelength region including the first maximum emission wavelengths MW1 of the first light-emitting elements 7-R, 7-G, and 7-B and the second maximum emission wavelength MW2 of the second light-emitting element 7-IR. With this configuration, the optical sensor 6 including the photoelectric conversion elements 8 can detect the various types of biological information based on the light L2 having the different wavelengths.

Figure 18:
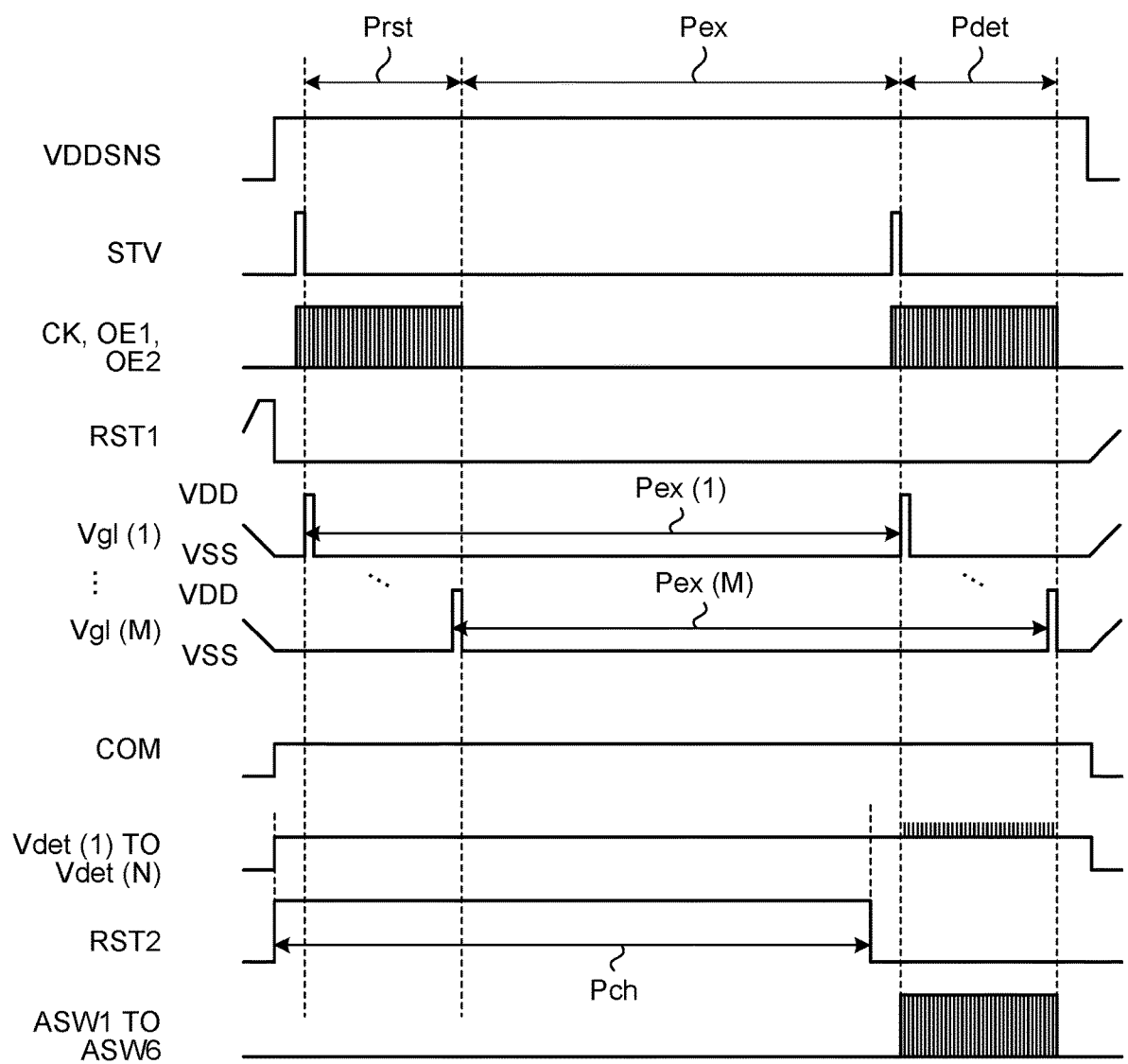
FIG. 18 is a timing waveform diagram illustrating an operation example of the optical sensor.
Figure 19:
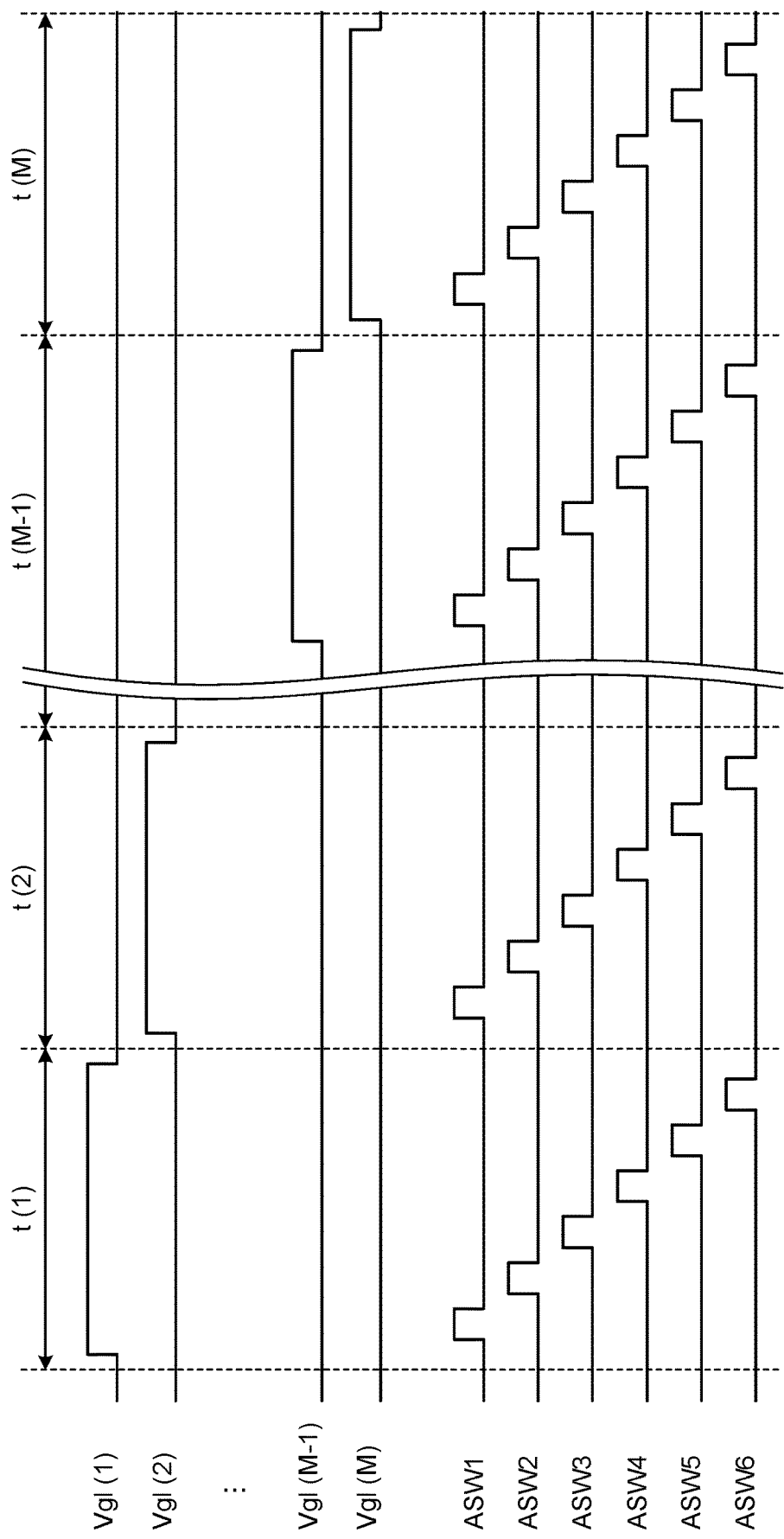
FIG. 19 is a timing waveform diagram illustrating an operation example during a reading period in FIG. 18.

The following describes an operation example of the detection apparatus 1. FIG. 18 is a timing waveform diagram illustrating an operation example of the optical sensor. FIG. 19 is a timing waveform diagram illustrating an operation example during the reading period in FIG. 18.

As illustrated in FIG. 18, the optical sensor 6 includes the reset period Prst, an exposure period Pex, and the reading period Pdet. The power supply circuit 162 supplies the sensor power supply signal VDDSNS to the photoelectric conversion elements 8 over the reset period Prst, the exposure period Pex, and the reading period Pdet. At a time before the reset period Prst starts, the detection control circuit 161 supplies the reference signal COM and the reset signal RST2 serving as a high-level voltage signal to the reset circuit 167. At this time, the reference signal COM is set to 0.75 V. The detection control circuit 161 supplies the start signal STV to the gate line drive circuit 165, and thus the reset period Prst starts.

During the reset period Prst, the gate line drive circuit 165 sequentially selects the sensor scan lines GLB based on the start signal STV, the clock signal CK, and the reset signal RST1. The gate line drive circuit 165 sequentially supplies the gate drive signals Vgl to the sensor scan lines GLB. The gate drive signal Vgl has a pulsed waveform having a power supply voltage VDD serving as a high-level voltage and a power supply voltage VSS serving as a low-level voltage. In FIG. 18, M (where M is, for example, 256) sensor scan lines GLB are provided, and the gate drive signals Vgl(1) . . . , Vgl(M) are sequentially supplied to the respective sensor scan lines GLB.

Thus, in the reset period Prst, the capacitive elements Ca of all the partial detection areas PAA are sequentially electrically coupled to the sensor signal lines SLB and are supplied with the reference signal COM. As a result, the capacitances of the capacitive elements Ca are reset.

The exposure period Pex starts after the gate drive signal Vgl(M) is supplied to the sensor scan line GLB. The actual exposure periods Pex(1), . . . , Pex(M) of the partial detection areas PAA corresponding to the sensor scan lines GLB differ from one another in their start timings and end timings. Each of the exposure periods Pex(1), . . . , Pex(M) starts when the gate drive signal Vgl changes from the power supply voltage VDD as the high-level voltage to the power supply voltage VSS as the low-level voltage in the reset period Prst. Each of the exposure periods Pex(1), . . . , Pex(M) ends when the gate drive signal Vgl changes from the power supply voltage VSS to the power supply voltage VDD in the reading period Pdet. The lengths of the exposure time of the exposure periods Pex(1), . . . , Pex(M) are equal.

A current flows correspondingly to the light emitted to the photoelectric conversion element 8 in each of the partial detection areas PAA in the exposure periods Pex. As a result, an electrical charge is stored in each of the capacitive elements Ca.

At a time before the reading period Pdet starts, the detection control circuit 161 sets the reset signal RST2 to a low-level voltage. This operation stops operation of the reset circuit 167. During the reading period Pdet, the gate line drive circuit 165 sequentially supplies the gate drive signals Vgl(1) . . . , Vgl(M) to the sensor scan lines GLB in the same manner as during the reset period Prst.

Specifically, as illustrated in FIG. 19, the gate line drive circuit 165 supplies the gate drive signal Vgl(1) serving as the high-level voltage (power supply voltage VDD) to the sensor scan line GLB(1) in a period t(1). In the period in which the gate drive signal Vgl(1) is at the high-level voltage (power supply voltage VDD), the detection control circuit 161 sequentially supplies selection signals ASW1, . . . , ASW6 to the signal line selection circuit 166. As a result, the sensor signal lines SLB of the partial detection areas PAA selected by the gate drive signal Vgl(1) are sequentially or simultaneously coupled to the detection circuit 163. As a result, the detection signal Vdet for each of the partial detection areas PAA is supplied to the detection circuit 163.

In the same manner, the gate line drive circuit 165 supplies the gate drive signals Vgl(2), . . . , Vgl(M−1), Vgl(M) at the high-level voltage to the sensor scan lines GLB(2), . . . , GLB(M−1), GLB(M) in periods t(2), . . . , t(M−1), t(M), respectively. That is, the gate line drive circuit 165 supplies the gate drive signal Vgl to the sensor scan line GLB in each of the periods t(1), t(2), . . . , t(M−1), t(M). The signal line selection circuit 166 sequentially selects the sensor signal lines SLB based on the selection signals ASW in each period in which the gate drive signal Vgl is set to the high-level voltage. The signal line selection circuit 166 sequentially couples each of the sensor signal lines SLB to one detection circuit 163. Thus, the optical sensor 6 can output the detection signals Vdet of all the partial detection areas PAA to the detection circuit 163 in the reading period Pdet.

Although FIG. 19 illustrates the example in which the gate line drive circuit 165 selects one of the sensor scan lines GLB in each of the periods t, the present disclosure is not limited to this example. The gate line drive circuit 165 may simultaneously select a predetermined number (equal to or greater than two) of the sensor scan lines GLB, and may sequentially supply the gate drive signal Vgl to each group of the predetermined number of the sensor scan lines GLB. The signal line selection circuit 166 may also simultaneously couple a predetermined number (equal to or greater than two) of the sensor signal lines SLB to the one detection circuit 163. Furthermore, the gate line drive circuit 165 may skip some of the sensor scan lines GLB and scan the remaining ones of the sensor scan lines GLB.

Figure 20:
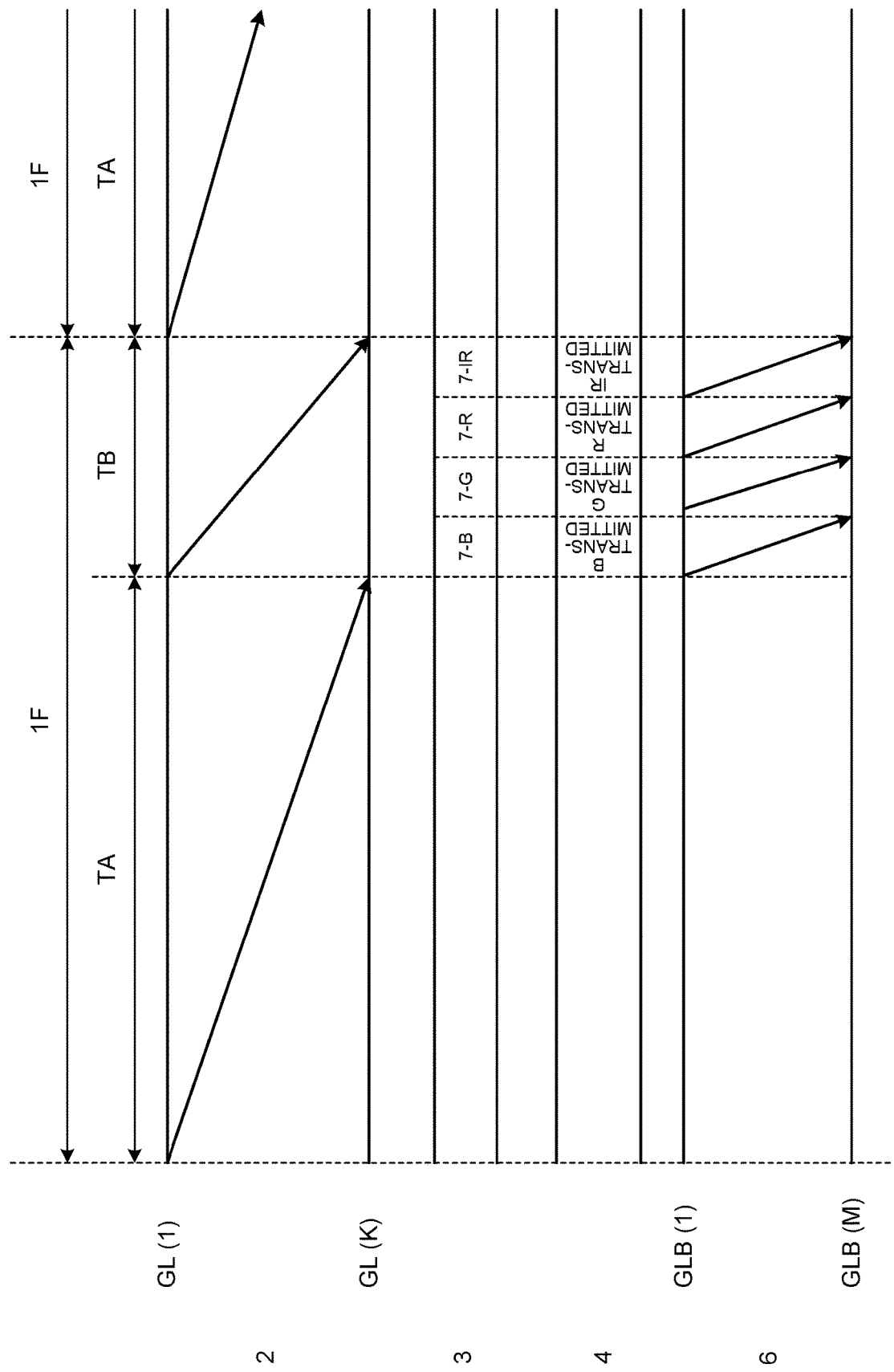
FIG. 20 is a timing waveform diagram illustrating an operation example of the display panel, the lighting device, the wavelength selection filter, and the optical sensor in the detection apparatus according to the first embodiment.
Figure 21:
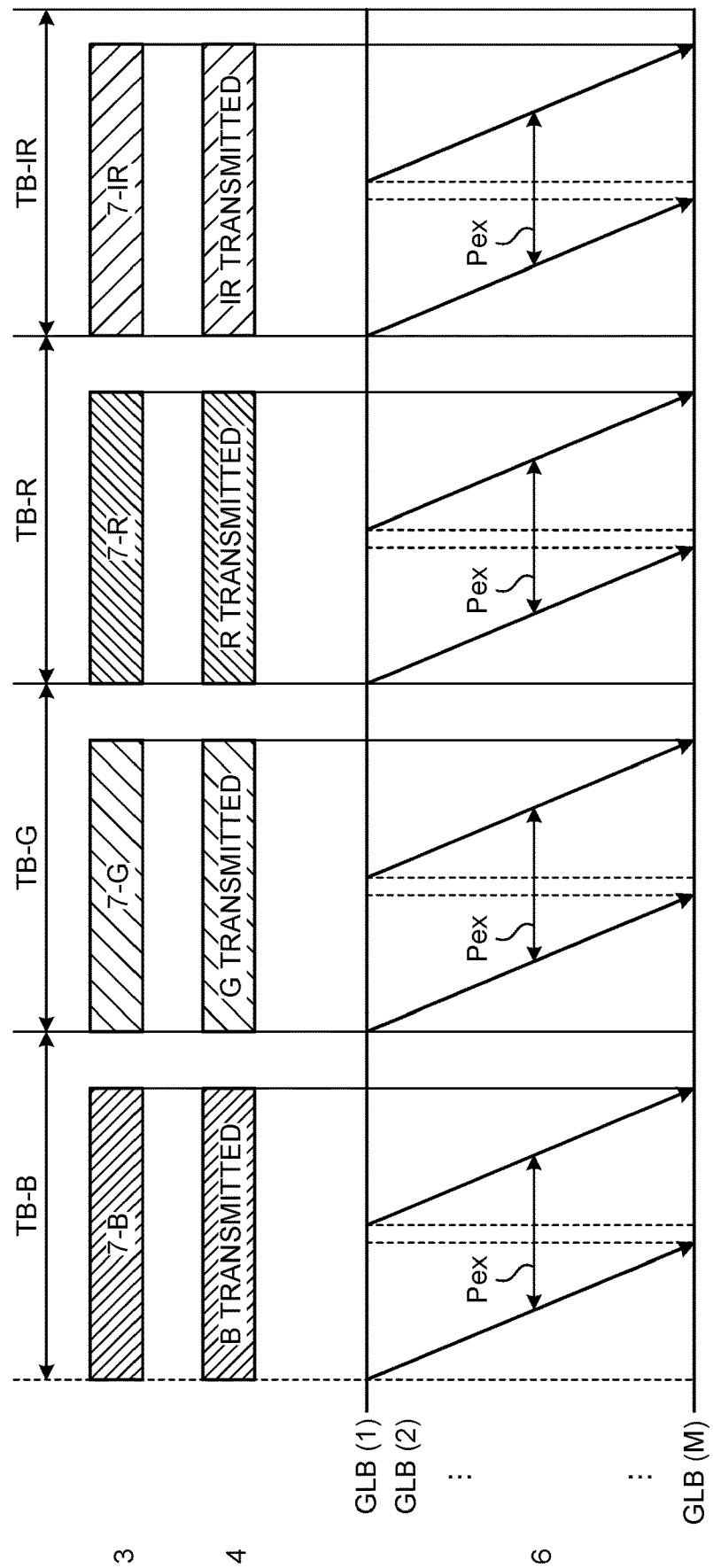
FIG. 21 is a timing waveform diagram illustrating a non-display period in FIG. 20 in an enlarged manner.

FIG. 20 is a timing waveform diagram illustrating an operation example of the display panel, the lighting device, the wavelength selection filter, and the optical sensor in the detection apparatus according to the first embodiment. FIG. 21 is a timing waveform diagram illustrating the non-display period in FIG. 20 in an enlarged manner.

The display panel 2 has the display period TA and the non-display period TB in one display frame 1F for displaying one image (one frame). The display period TA is a period in which the image signal OP is supplied to each of the pixels PX and the pixels PX display the image. The non-display period TB is, for example, a vertical blanking period.

The display panel 2 performs display of the display frames 1F by alternately repeating the display period TA and the non-display period TB.

In the display period TA, the lighting device 3 turns on the first light-emitting elements 7-R, 7-G, and 7-B to emit the visible light L1. In the display period TA, the lighting device 3 does not turn on the second light-emitting element 7-IR. The display panel 2 performs the display using the light L1. The optical sensor 6 does not perform the detection using the photoelectric conversion elements 8 during the display period TA. Specifically, during the display period TA, the optical sensor 6 does not execute at least the exposure of the exposure period Pex among the reset period Prst, the exposure period Pex, and the reading period Pdet. At this time, the wavelength selection filter 4 does not transmit the light L2 of the visible light and the infrared light. As a result, the light L2 is restrained from being incident on the photoelectric conversion elements 8 of the optical sensor 6.

The lighting device 3, the wavelength selection filter 4, the optical element 5 (refer to FIG. 1), and the optical sensor 6 are used to detect the various types of biological information during the non-display period TB. During the non-display period TB, the display panel 2 is in a transmitting state of transmitting the light L1 and L2 in a wavelength region ranging from the visible light to the infrared light. As illustrated in FIG. 21, the non-display period TB (detection period) includes first detection periods TB-B, TB-G, and TB-R and a second detection period TB-IR provided in a time-division manner. The detection operations of the first detection periods TB-B, TB-G, and TB-R and the second detection period TB-IR are sequentially executed in the order as listed. However, the order of the detection periods may be changed as appropriate.

the lighting device 3 respectively turns on the first light-emitting elements 7-B, 7-G, and 7-R and the second light-emitting element 7-IR in the first detection periods TB-B, TB-G, and TB-R and the second detection period TB-IR, in a time-division manner. Specifically, the lighting device 3 turns on the first light-emitting element 7-B and turns off the first light-emitting elements 7-G and 7-R and the second light-emitting element 7-IR during the first detection period TB-B. By this operation, the lighting device 3 causes the first light-emitting element 7-B to emit the visible (for example, blue) light L1 (first light).

In the same manner, the lighting device 3 causes the first light-emitting elements 7-G and 7-R to emit the visible (for example, green and red) light L1 (first light) during the first detection periods TB-G and TB-R, respectively. During the second detection period TB-IR, the lighting device 3 causes the second light-emitting element 7-IR to emit the infrared light L1, more preferably, the near-infrared light L1 (second light).

The wavelength selection filter 4 varies the transmission band for transmitting the light L2 and the non-transmission band for not transmitting the light L2 in the first detection periods TB-B, TB-G, and TB-R and the second detection period TB-IR in a time-division manner. The wavelength selection filter 4 is in the transmitting state for the wavelength region including the first maximum emission wavelength MW1 of the first light-emitting element 7-B (refer to FIG. 17) during the first detection period TB-B.

In the same manner, the wavelength selection filter 4 is in the transmitting state for the wavelength regions including the first maximum emission wavelengths MW1 of the first light-emitting elements 7-G and 7-R (refer to FIG. 17) during the first detection periods TB-G and TB-R, respectively. The wavelength selection filter 4 is in the transmitting state for the wavelength region including the second maximum emission wavelength MW2 of the second light-emitting element 7-IR (refer to FIG. 17) during the second detection period TB-IR. As a result, in the first detection periods TB-B, TB-G, and TB-R and the second detection period TB-IR, the light L2 having the wavelengths different from one another is incident on the optical sensor 6 through the display panel 2, the opening OA of the lighting device 3, the wavelength selection filter 4, and the light-transmitting area 51 of the optical element 5.

During each period of the first detection periods TB-B, TB-G, and TB-R and the second detection period TB-IR, the optical sensor 6 executes the operations of the reset period Prst, the exposure period Pex, and the reading period Pdet. Specifically, during the first detection period TB-B, the optical sensor 6 executes the exposure of the exposure period Pex by sequentially scanning the sensor scan lines GLB(1), GLB(2), . . . , GLB(M). During the reading period Pdet, the gate line drive circuit 165 sequentially scans the sensor scan lines GLB, so that each of the photoelectric conversion elements 8 outputs a signal based on the visible (for example, blue) light L2 to the detection circuit 163.

In the same manner, during the first detection periods TB-G and TB-R, each of the photoelectric conversion elements 8 of the optical sensor 6 outputs a signal based on the visible (for example, green and red) light L2 to the detection circuit 163. As a result, the optical sensor 6 can detect the fingerprint of the finger Fg based on the visible light L2 in the first detection periods TB-B, TB-G, and TB-R. During the second detection period TB-IR, each of the photoelectric conversion elements 8 of the optical sensor 6 outputs a signal based on the infrared (for example, near-infrared) light L2 to the detection circuit 163. In the second detection period TB-IR, the optical sensor 6 can detect the blood vessel image (vein pattern) based on the near-infrared light L2.

The operation example illustrated in FIGS. 20 and 21 is merely an example and may be changed as appropriate. For example, the detection apparatus 1 may perform the detection based on the light L2 having a different wavelength for each of the display frames 1F. That is, the lighting device 3 may turn on any one type of light-emitting element among the first light-emitting elements 7-B, 7-G, and 7-R and the second light-emitting element 7-IR during the non-display period TB of each of the display frames 1F. When the detection apparatus 1 performs the detection with the visible light L2, the detection apparatus 1 only needs to turn on at least one of the first light-emitting elements 7-B, 7-G, and 7-R during the non-display period TB. In other words, in the first light-emitting element 7-B, 7-G, or 7-R, unused one for the detection may be included.

As described above, the detection apparatus 1 includes the display panel 2, the optical sensor 6, and the lighting device 3. The display panel 2 includes the array substrate SUB1, the counter substrate SUB2 facing the array substrate SUB1, and the liquid crystal layer LC provided between the array substrate SUB1 and the counter substrate SUB2. The optical sensor 6 includes the sensor base member 61 and the photoelectric conversion elements 8 that are provided on the sensor base member 61 and each output the signal corresponding to the light L2 emitted thereto, and faces the array substrate SUB1 of the display panel 2. The lighting device 3 includes the first light-emitting elements 7-R, 7-G, and 7-B that emit the first light having the first maximum emission wavelengths MW1 and the second light-emitting elements 7-IR that emit the second light having the second maximum emission wavelength MW2. Each of the photoelectric conversion elements 8 has the responsivity in the wavelength region including the wavelength region of the first light and the wavelength region of the second light.

Since each of the photoelectric conversion elements 8 of the optical sensor 6 has the responsivity in the wide wavelength region, the optical sensor 6 can detect the various different types of biological information based on the light L2 having different wavelengths that has been emitted from the light-emitting elements 7.

The first light-emitting elements 7-R, 7-G, and 7-B and the second light-emitting elements 7-IR emit the first light and the second light at respective different wavelengths in a time-division manner. The detection apparatus 1 can detect the various types of biological information for each different wavelength region of the light L2 by driving the lighting device 3, the wavelength selection filter 4, and the optical sensor 6 in a time-division manner.

The wavelength selection filter 4 can vary the transmitting state for the light L2 incident on the optical sensor 6 according to the biological information on the detection target. That is, a component of the light L2 reflected by the finger Fg in a predetermined wavelength region suitable for detecting the biological information on the detection target is made incident on the optical sensor 6. The wavelength selection filter 4 can restrain a component of the light L2 not in the predetermined wavelength region from being incident on the optical sensor 6. As a result, the detection apparatus 1 can improve the detection accuracy of the various different types of biological information.

Second Embodiment

Figure 22:
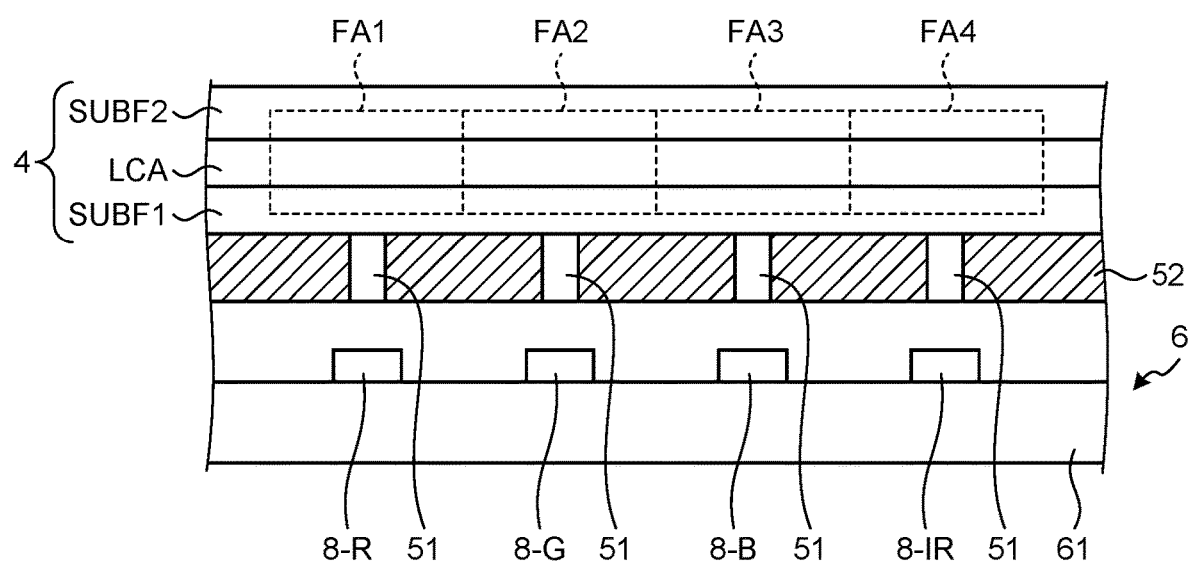
FIG. 22 is a sectional view schematically illustrating an arrangement relation between the wavelength selection filter, the light-emitting elements, and the optical sensor of the detection apparatus according to a second embodiment.
Figure 23:
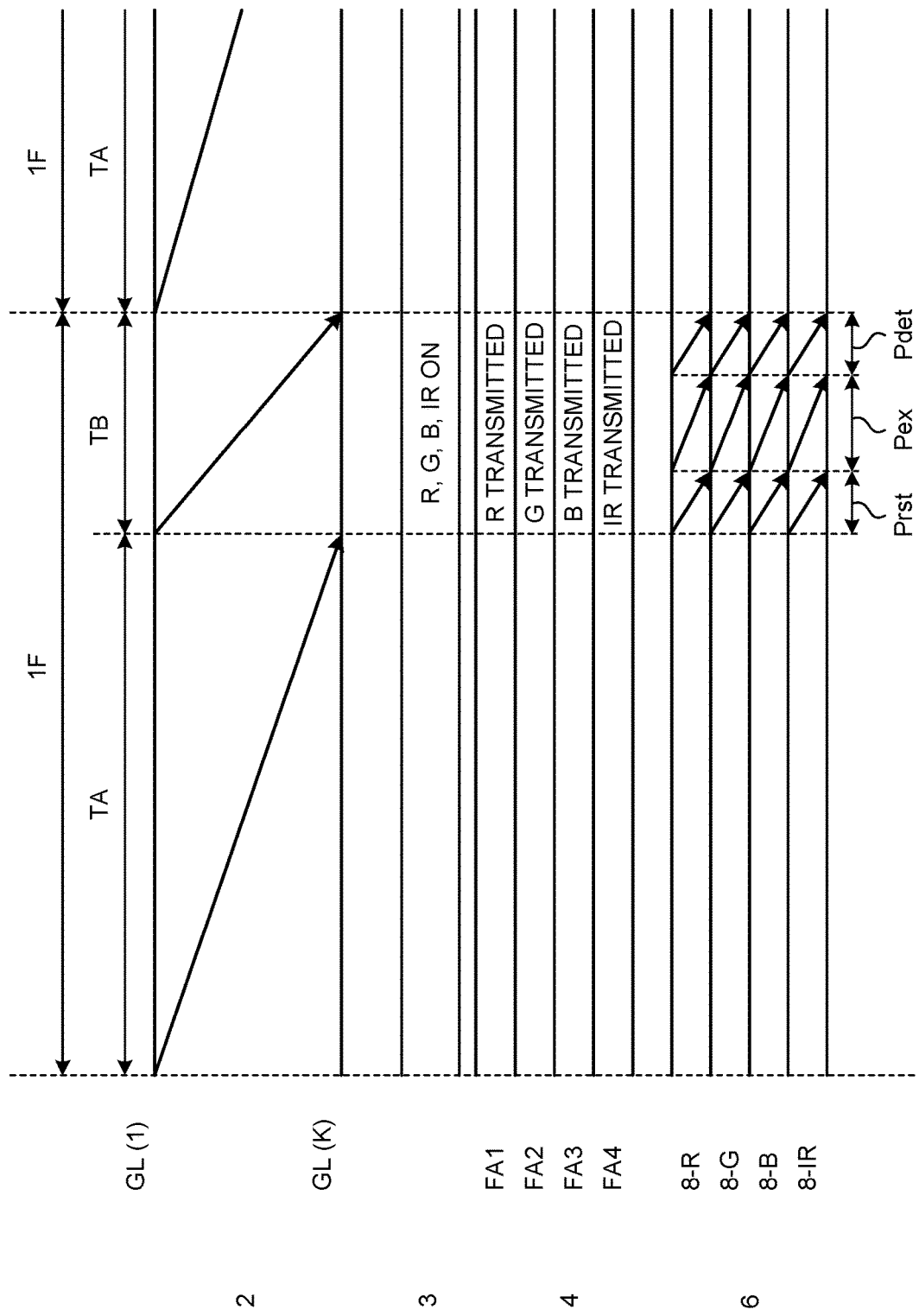
FIG. 23 is a timing waveform diagram illustrating an operation example of the detection apparatus according to the second embodiment.

FIG. 22 is a sectional view schematically illustrating an arrangement relation between the wavelength selection filter, the light-emitting elements, and the optical sensor of the detection apparatus according to a second embodiment. FIG. 23 is a timing waveform diagram illustrating an operation example of the detection apparatus according to the second embodiment. While FIG. 22 does not illustrate the display panel 2 and the lighting device 3, the lighting device 3 and the display panel 2 are stacked upon the wavelength selection filter 4 in the same manner as in the first embodiment. In the following description, the components described in the above-described embodiment will be denoted by the same reference numerals and will not be described.

As illustrated in FIG. 22, the wavelength selection filter 4 varies the wavelength region for transmitting the light L2 for each of unit filter areas FA1, FA2, FA3, and FA4. Specifically, the wavelength selection filter 4 is in the transmitting state for the wavelength region including the first maximum emission wavelength MW1 of the first light-emitting element 7-R in the unit filter area FA1. That is, the unit filter area FA1 transmits the light L2 in the wavelength region approximately from 580 nm to 700 nm (for example, the red light L2), and does not transmit the light L2 in a wavelength region shorter than 580 nm and in a wavelength region longer than 700 nm.

In the same manner, the wavelength selection filter 4 is in the transmitting state for the wavelength region including the first maximum emission wavelength MW1 of the first light-emitting element 7-G in the unit filter area FA2. As a result, for example, the green light L2 passes through the unit filter area FA2. The wavelength selection filter 4 is in the transmitting state for the wavelength region including the first maximum emission wavelength MW1 of the first light-emitting element 7-B in the unit filter area FA3. For example, the blue light L2 passes through the unit filter area FA3. The wavelength selection filter 4 is in the transmitting state for the wavelength region including the second maximum emission wavelength MW2 of the second light-emitting element 7-IR in the unit filter area FA4. For example, the near-infrared light L2 passes through the unit filter area FA4.

The photoelectric conversion element 8 includes first photoelectric conversion elements 8-R, 8-G, and 8-B and a second photoelectric conversion element 8-IR. The unit filter areas FA1, FA2, FA3, and FA4 are provided in positions overlapping the first photoelectric conversion elements 8-R, 8-G, and 8-B and the second photoelectric conversion element 8-IR, respectively. The first photoelectric conversion elements 8-R, 8-G, and 8-B and the second photoelectric conversion element 8-IR may all be made of the same conversion element. In this case, the first photoelectric conversion elements 8-R, 8-G, and 8-B and the second photoelectric conversion element 8-IR have the responsivity in the region ranging from the visible light region to the near-infrared region in the same manner as in FIG. 17. Alternatively, the first photoelectric conversion elements 8-R, 8-G, and 8-B and the second photoelectric conversion element 8-IR may have the responsivity in wavelength regions different from one another.

The first photoelectric conversion element 8-R receives the light L2 (for example, the red light L2) that has passed through the unit filter area FA1 and the light-transmitting area 51, and outputs a signal based on the light L2 to the detection circuit 163. In the same manner, the first photoelectric conversion element 8-G receives the light L2 (for example, the green light L2) that has passed through the unit filter area FA2 and the light-transmitting area 51, and outputs a signal based on the light L2 to the detection circuit 163. The first photoelectric conversion element 8-B receives the light L2 (for example, the blue light L2) that has passed through the unit filter area FA3 and the light-transmitting area 51, and outputs a signal based on the light L2 to the detection circuit 163. The second photoelectric conversion element 8-IR receives the light L2 (for example, the near-infrared light L2) that has passed through the unit filter area FA4 and the light-transmitting area 51, and outputs a signal based on the light L2 to the detection circuit 163.

With the above-described configuration, the detection apparatus 1 can use the first photoelectric conversion elements 8-R, 8-G, and 8-B to detect the fingerprint of the finger Fg, and can use the second photoelectric conversion element 8-IR to detect the blood vessel image (vein pattern). That is, the detection apparatus 1 can detect the various types of biological information based on the light L2 having a different wavelength for each of the unit filter areas FA in the plan view.

As illustrated in FIG. 23, the lighting device 3 turns on the first light-emitting elements 7-R, 7-G, and 7-B and the second light-emitting element 7-IR during the same non-display period TB (detection period). As a result, during the same non-display period TB (detection period), the first light-emitting elements 7-R, 7-G, and 7-B emit the light L1 (first light) having the wavelengths different from one another, and the second light-emitting element 7-IR emits the near-infrared light L1 (second light).

During the non-display period TB, the wavelength selection filter 4 allows the wavelength regions including the first maximum emission wavelengths MW1 of the first light-emitting elements 7-R, 7-G, and 7-B to be transmitted through the unit filter areas FA1, FA2, and FA3 (first areas), respectively. The wavelength selection filter 4 also allows the wavelength region including the second maximum emission wavelength MW2 of the second light-emitting element 7-IR to be transmitted through the unit filter area FA4 (second area).

During the non-display period TB, the optical sensor 6 executes the operations of the reset periods Prst, the exposure periods Pex, and the reading periods Pdet of the first photoelectric conversion elements 8-R, 8-G, and 8-B and the second photoelectric conversion element 8-IR. The resets of the reset periods Prst of the first photoelectric conversion elements 8-R, 8-G, and 8-B and the second photoelectric conversion element 8-IR are executed in the same period. The exposures of the exposure periods Pex of the first photoelectric conversion elements 8-R, 8-G, and 8-B and the second photoelectric conversion element 8-IR are executed in the same period. The reading operations of the reading periods Pdet of the first photoelectric conversion elements 8-R, 8-G, and 8-B and the second photoelectric conversion element 8-IR are executed in the same period.

As a result, in the same non-display period TB, the first photoelectric conversion elements 8-R, 8-G, and 8-B output the signals based on the visible light L2 (first light) to the detection circuit 163, and the second photoelectric conversion element 8-IR outputs the signal based on the near-infrared light L2 (second light) to the detection circuit 163.

In the second embodiment, the wavelength selection filter 4 can vary the wavelength region for transmitting the light L2 for each of the unit filter areas FA1, FA2, FA3, and FA4. Consequently, during the non-display period TB, the first light-emitting elements 7-R, 7-G, and 7-B and the second light-emitting element 7-IR can be simultaneously turned on, and the first photoelectric conversion elements 8-R, 8-G, and 8-B and the second photoelectric conversion element 8-IR can simultaneously detect the light L2 having the wavelengths different from one another. As a result, the detection apparatus 1 can detect the different types of biological information during the same period. In addition, since the light-emitting elements 7 need not be turned on in a time-division manner in the non-display period TB, the control of the lighting device 3 can be simplified.

Figure 24:
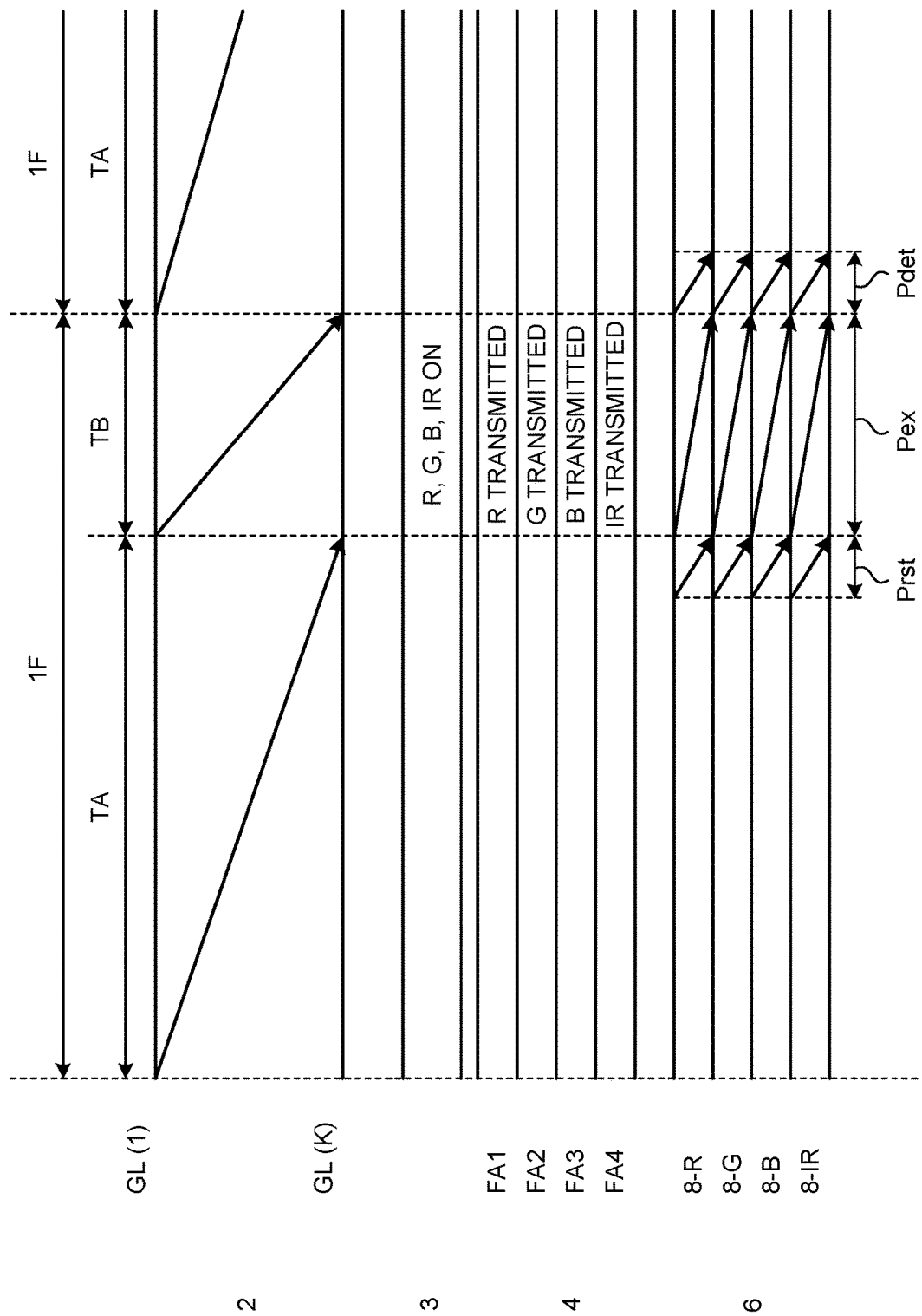
FIG. 24 is a timing waveform diagram illustrating an operation example of the detection apparatus according to a second modification of the second embodiment.

FIG. 24 is a timing waveform diagram illustrating an operation example of the detection apparatus according to a second modification of the second embodiment. While in FIG. 23, the optical sensor 6 executes the operations of the reset period Prst, the exposure period Pex, and the reading period Pdet during the non-display period TB, the present disclosure is not limited thereto. As illustrated in FIG. 24, in the second modification, the reset period Prst overlaps a part of the display period TA of the display panel 2, and the reading period Pdet overlaps a part of the display period TA of the next display frame 1F.

As a result, the exposure period Pex of each of the photoelectric conversion elements 8 can be increased and the detection accuracy of the optical sensor 6 can be increased as compared with the second embodiment illustrated in FIG. 23. The operation example of the second modification illustrated in FIG. 24 can also be applied to the detection apparatus 1 of the first embodiment. That is, the reset period Prst of the first detection period TB-B illustrated in FIG. 21 may overlap a part of the display period TA, and the reading period Pdet of the second detection period TB-IR may overlap a part of the display period TA of the next display frame 1F.

Third Embodiment

Figure 25:
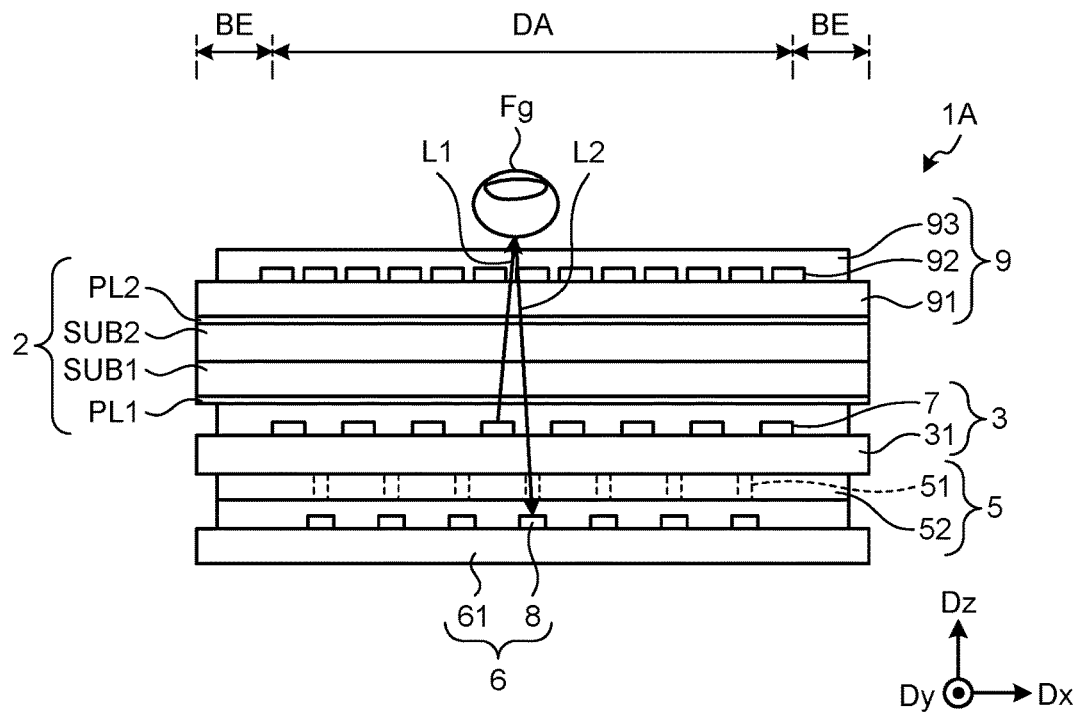
FIG. 25 is a sectional view illustrating a schematic sectional configuration of a detection apparatus according to a third embodiment.
Figure 26:
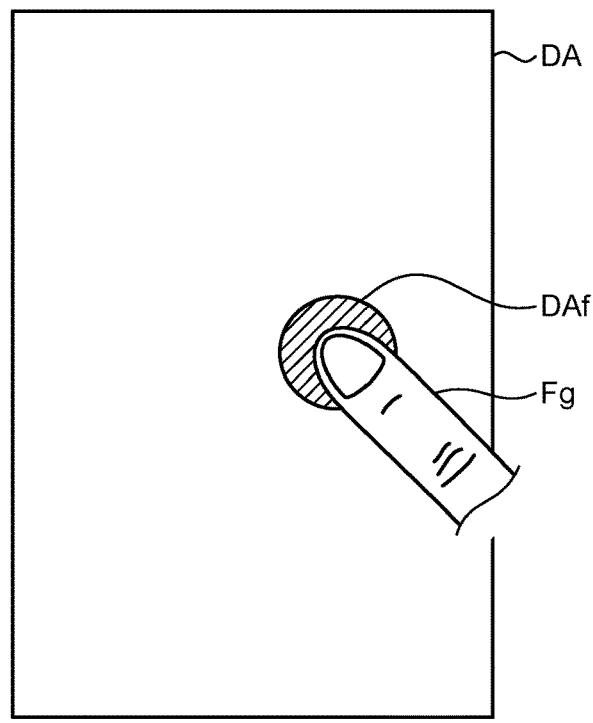
FIG. 26 is a plan view schematically illustrating the display area of the display panel according to the third embodiment.
Figure 27:
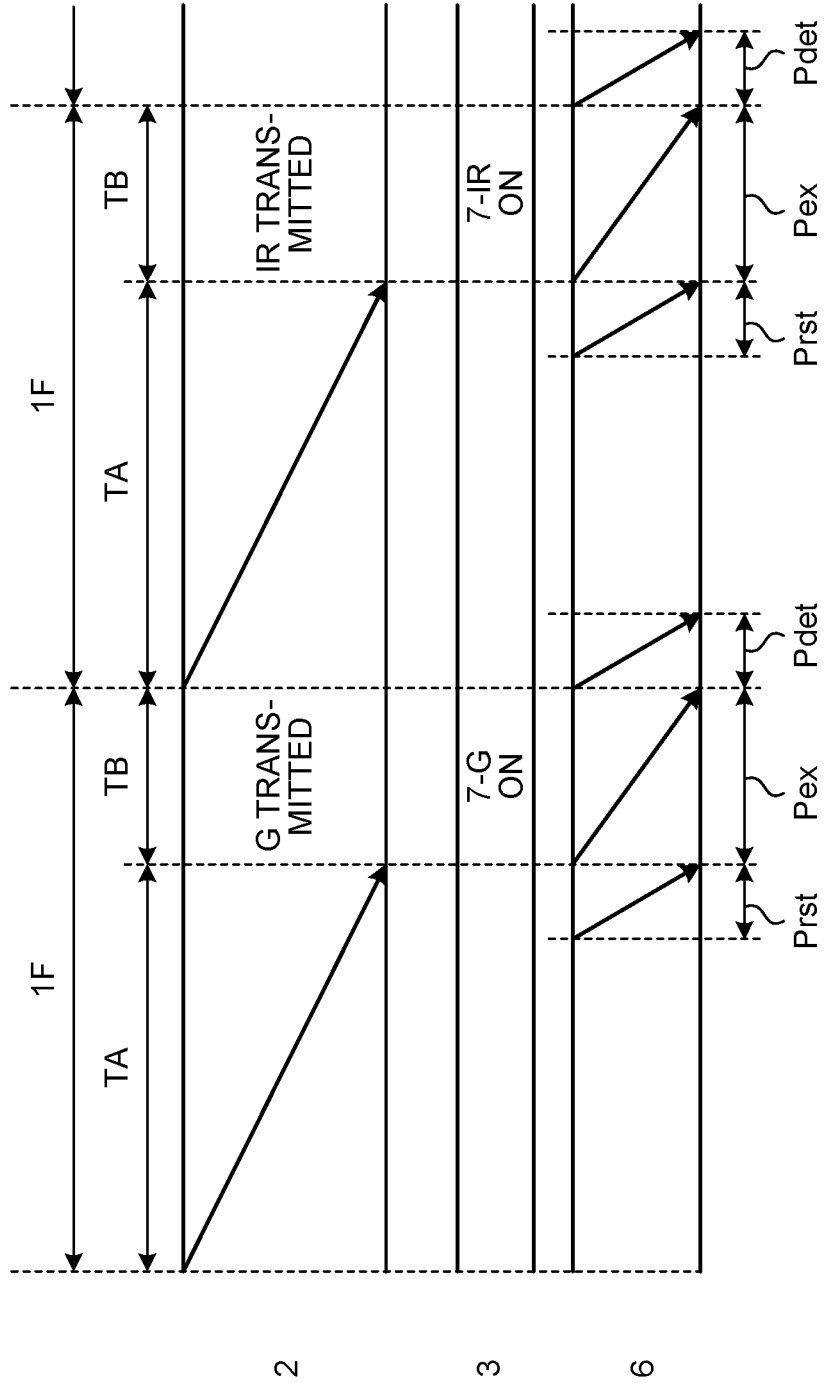
FIG. 27 is a timing waveform diagram illustrating an operation example of the detection apparatus according to the third embodiment.

FIG. 25 is a sectional view illustrating a schematic sectional configuration of a detection apparatus according to a third embodiment. FIG. 26 is a plan view schematically illustrating the display area of the display panel according to the third embodiment. FIG. 27 is a timing waveform diagram illustrating an operation example of the detection apparatus according to the third embodiment.

As illustrated in FIG. 25, a detection apparatus 1A according to the third embodiment further includes a touch panel 9 that detects the finger Fg in contact with or proximity to a detection surface. The touch panel 9 is provided upon the second polarizing plate PL2 of the display panel 2. The touch panel 9 may be of a self-capacitive type or a mutual capacitive type. The touch panel 9 may be integrally formed with the display panel 2. That is, parts of a base member and electrodes of the display panel 2 may also be used as a base member and electrodes of the touch panel 9.

The touch panel 9 includes a base member 91, a plurality of detection electrodes 92, and a protective layer 93. The base member 91 is formed of a light-transmitting insulating material and is formed using, for example, glass or a resin material. The detection electrodes 92 are provided on the base member 91 and are formed of a light-transmitting conductive material such as ITO or IZO. The protective layer 93 covers the detection electrodes 92. A surface of the protective layer 93 serves as the detection surface of the touch panel 9. However, a cover glass may be provided on the touch panel 9. In this case, a surface of the cover glass serves as the detection surface.

In the present embodiment, the display panel 2 also serves as the wavelength selection filter 4. That is, in the detection apparatus 1A, the wavelength selection filter 4 is not included, and the optical sensor 6, the optical element 5, the lighting device 3, the display panel 2, and the touch panel 9 are stacked in the third direction Dz in the order as listed.

As illustrated in FIG. 26, the display panel 2 displays an image in the display area DA. When the finger Fg is in contact with or proximity to the detection surface, the display panel 2 acquires position information on the finger Fg from the touch panel 9. The display panel 2 applies a voltage to the liquid crystal layer LC such that the light L2 in the predetermined wavelength region to be incident on the photoelectric conversion element 8 is transmitted in an overlapping area DAf of the display area DA overlapping the finger Fg. The display panel 2 drives the liquid crystal layer LC based on the image signal OP in a portion of the display area DA other than the overlapping area DAf, and thus makes the transmitting state of the light L1 and L2 in the overlapping area DAf different from that in the display area DA.

As a result, in the portion of the display area DA not overlapping the finger Fg, the image is displayed based on the light L1 emitted from the light-emitting elements 7. The light-emitting element 7 provided in a position overlapping the overlapping area DAf emits the light L1 for detection different from the light L1 for display. The light-emitting element 7 emits the visible or near-infrared light L1 depending on the biological information on the detection target. In the overlapping area DAf, the light L1 passes through the display panel 2 and the touch panel 9 and is incident on the finger Fg. The light L2 reflected by the finger Fg passes through the touch panel 9, the display panel 2, the lighting device 3, and the light-transmitting area 51 of the optical element 5 and is incident on the photoelectric conversion element 8.

As illustrated in FIG. 27, the display panel 2 changes the wavelength region for transmitting the light L1 and L2 for detection for each of the display frames 1F. During the non-display period TB of the display frame 1F, the lighting device 3 turns on the first light-emitting element 7-G, and the display panel 2 transmits the visible light (for example, the green light) in the overlapping area DAf. During the non-display period TB of the next display frame 1F, the lighting device 3 turns on the second light-emitting element 7-IR, and the display panel 2 transmits the near-infrared light in the overlapping area DAf. Since the display panel 2 transmits the light L1 and L2 for detection only in the overlapping area DAf, the detections may be simultaneously performed during the display period TA.

As a result, the detection apparatus 1A can both display the image on the display panel 2 and detect the biological information using the optical sensor 6. Since the display panel 2 also serves as the wavelength selection filter 4, the detection apparatus 1A can be thinner than in the first and the second embodiments.

Fourth Embodiment

Figure 28:
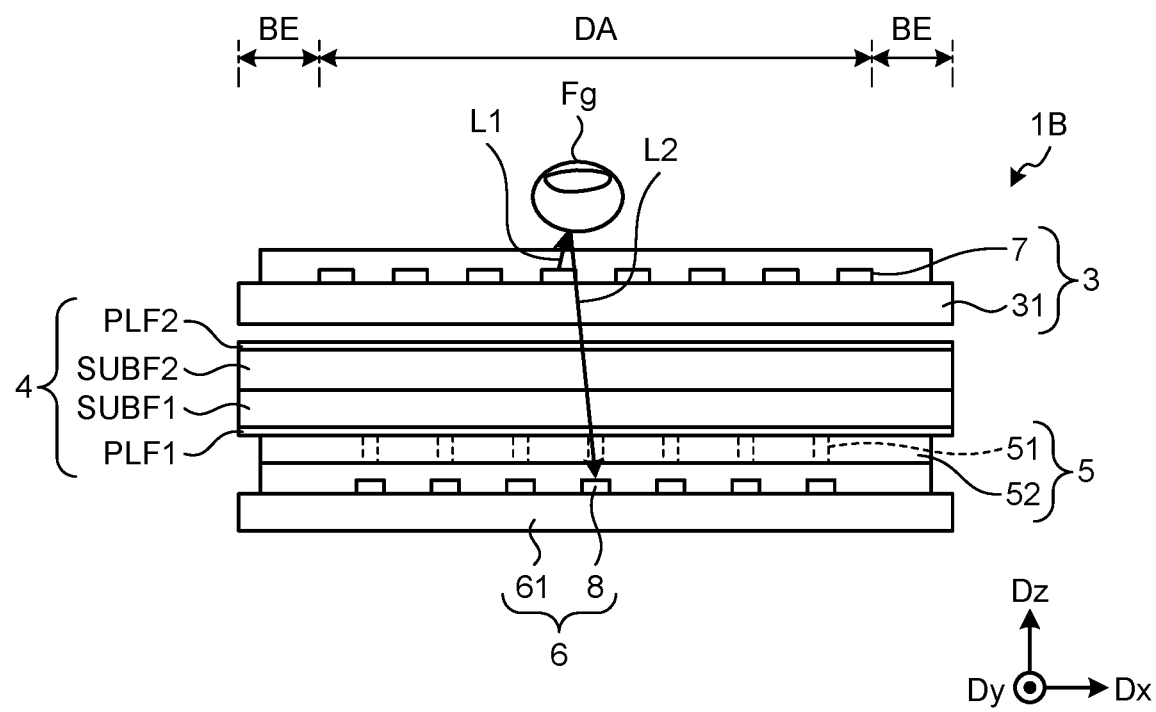
FIG. 28 is a sectional view illustrating a schematic sectional configuration of a detection apparatus according to a fourth embodiment.

FIG. 28 is a sectional view illustrating a schematic sectional configuration of a detection apparatus according to a fourth embodiment. As illustrated in FIG. 28, a detection apparatus 1B includes the lighting device 3, the wavelength selection filter 4, the optical element 5, and the optical sensor 6. The detection apparatus 1B does not include the display panel 2, unlike the first to the third embodiments.

Also in the present embodiment, the light-emitting elements 7 include the first light-emitting elements 7-R, 7-G, and 7-B and the second light-emitting elements 7-IR that emit the light having the different wavelengths. In the same manner as in FIG. 17, each of the photoelectric conversion elements 8 has the responsivity in the wavelength region including the wavelength regions of the light L1 (first light) emitted from the first light-emitting elements 7-R, 7-G, and 7-B and the wavelength region of the light L2 (second light) emitted from the second light-emitting element 7-IR.

In the detection apparatus 1B, in the same manner as the example illustrated in FIG. 20, the first light-emitting elements 7-R, 7-G, and 7-B and the second light-emitting elements 7-IR can emit the light in a time-division manner, and the photoelectric conversion elements 8 can detect the biological information based on the light L2 having a different wavelength for each period. In this case, the detection apparatus 1B need not include the wavelength selection filter 4, and the lighting device 3 may be provided on the upper side of the optical element 5.

Alternatively, in the detection apparatus 1B, in the same manner as the example illustrated in FIG. 23, the first light-emitting elements 7-R, 7-G, and 7-B and the second light-emitting elements 7-IR may simultaneously emit the light, and the wavelength selection filter 4 may vary the wavelength region for transmitting the light for each of the unit filter areas FA. The photoelectric conversion element 8 can detect the biological information based on the light L2 having a different wavelength for each of the unit filter areas FA.

Figure 29:
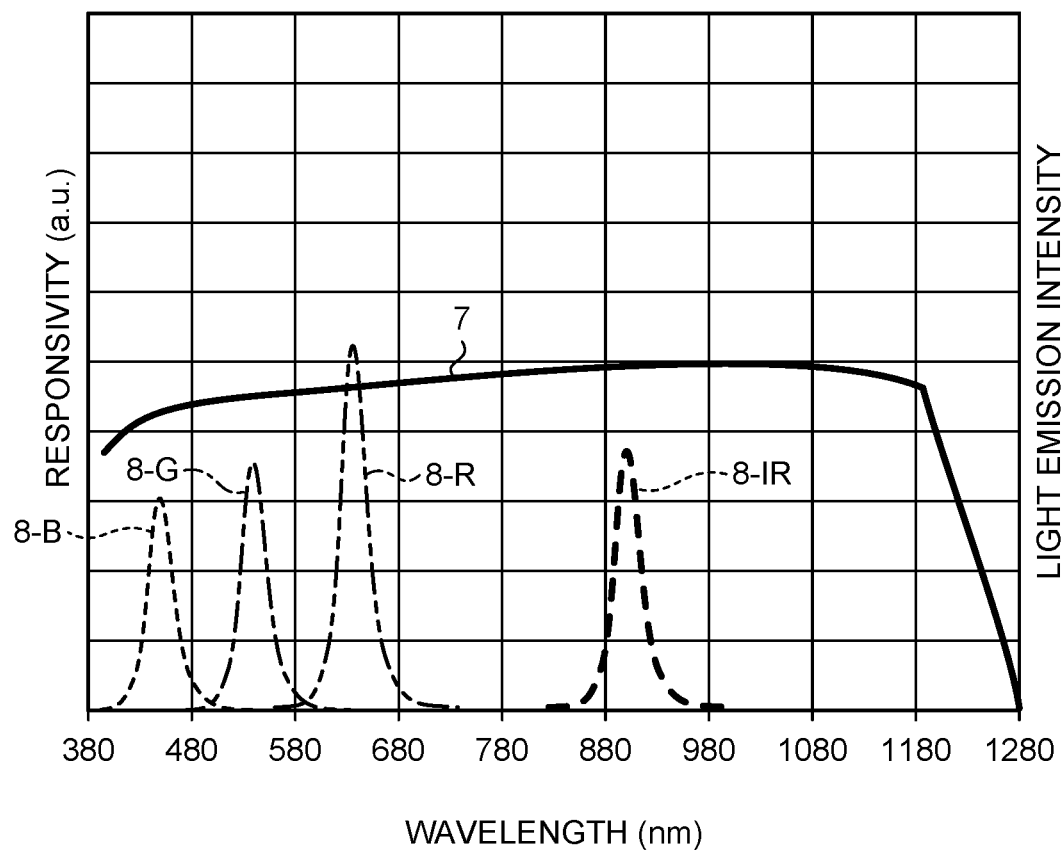
FIG. 29 is a graph illustrating relations of the responsivity of the photoelectric conversion element and the light emission intensity of the light-emitting elements with the wavelength in the detection apparatus according to a third modification of the fourth embodiment.

FIG. 29 is a graph illustrating relations of the responsivity of the photoelectric conversion element and the light emission intensity of the light-emitting elements with the wavelength in the detection apparatus according to a third modification of the fourth embodiment. As illustrated in FIG. 29, the light-emitting elements 7 of the detection apparatus 1B have the light emission intensity in the region ranging from the visible light region to the near-infrared region. The photoelectric conversion elements 8 include the first photoelectric conversion elements 8-B, 8-G, and 8-R and the second photoelectric conversion elements 8-IR. The first photoelectric conversion elements 8-B, 8-G, and 8-R have the responsivity in the visible light region. The second photoelectric conversion elements 8-IR have the responsivity in the near-infrared region.

The first photoelectric conversion elements 8-B, 8-G, and 8-R and the second photoelectric conversion elements 8-IR can receive light in wavelength regions different from one another during the same detection period. More specifically, the first photoelectric conversion elements 8-B, 8-G, and 8-R and the second photoelectric conversion elements 8-IR can detect the biological information by receiving the light L2 in wavelength regions having the responsivity of the respective beams of the light L1 emitted from the light-emitting elements 7.

In this modification, the detection apparatus 1B need not include the wavelength selection filter 4.

Although the preferred embodiments of the present disclosure has been described above, the present disclosure is not limited to the embodiment described above. The content disclosed in the embodiment is merely an example, and can be variously modified within the scope not departing from the gist of the present disclosure. Any modifications appropriately made within the scope not departing from the gist of the present disclosure also naturally belong to the technical scope of the present disclosure.

What is claimed is:

1. A detection apparatus comprising:
   an optical sensor comprising a sensor base member and a plurality of photoelectric conversion elements that are provided on the sensor base member and each of which is configured to output a signal corresponding to light emitted to the photoelectric conversion element;
   a lighting device comprising a plurality of first light-emitting elements configured to emit first light having a first maximum emission wavelength and a plurality of second light-emitting elements configured to emit second light having a second maximum emission wavelength, toward a front side of the detection apparatus, the front side being a side opposite to the optical sensor in a first direction orthogonal to the sensor base member; and
   a wavelength selection filter provided between the optical sensor and the lighting device in the first direction and that faces the photoelectric conversion elements, wherein
   each of the photoelectric conversion elements has responsivity in a wavelength region including a wavelength region of the first light and a wavelength region of the second light,
   the first light-emitting elements and the second light-emitting elements are configured to emit the first light and the second light at respective different wavelengths in a time-division manner, and the wavelength selection filter is configured to vary a transmission band for transmitting light incident on the photoelectric conversion elements and a non-transmission band for not transmitting the light in a time-division manner.

2. The detection apparatus according to claim 1, wherein the first light-emitting elements are configured to emit the first light in a visible light region, and the second light-emitting elements are configured to emit the second light in a near-infrared region.

3. The detection apparatus according to claim 1, wherein the optical sensor is configured to perform detection using the photoelectric conversion elements in each of a plurality of detection periods provided in a time-division manner,
   during a first detection period, the lighting device emits the first light using the first light-emitting elements, and the wavelength selection filter is in a transmitting state for a wavelength region including the first maximum emission wavelength,
   during a second detection period, the lighting device emits the second light using the second light-emitting elements, and the wavelength selection filter is in the transmitting state for a wavelength region including the second maximum emission wavelength, and
   each of the photoelectric conversion elements outputs a signal based on the first light to a detection circuit during the first detection period and outputs a signal based on the second light to the detection circuit during the second detection period.

4. The detection apparatus according to claim 1, comprising a liquid crystal display panel on a side opposite to a surface of the lighting device facing the optical sensor, the liquid crystal display panel comprising an array substrate, a counter substrate facing the array substrate, and a liquid crystal layer provided between the array substrate and the counter substrate, wherein
   the liquid crystal layer is configured to transmit light incident on the photoelectric conversion elements in a partial area of a display area.

5. The detection apparatus according to claim 4, further comprising a touch panel configured to detect an object in contact with or proximity to a detection surface, wherein
   the liquid crystal display panel is configured to transmit the light incident on the photoelectric conversion elements in an overlapping area of the display area where the object is in contact with or proximity to the detection surface.

6. The detection apparatus according to claim 4, wherein
   the optical sensor comprises capacitors coupled to the photoelectric conversion elements and sensor signal lines coupled to the photoelectric conversion elements through switching elements,
   the liquid crystal display panel is configured to execute operations of a display period and a non-display period in a time-division manner, and
   an exposure period in which the sensor signal lines are in a decoupled state from the photoelectric conversion elements overlaps the non-display period of the liquid crystal display panel.

7. The detection apparatus according to claim 6, wherein a reset period in which a reference potential is supplied to the capacitors through the sensor signal lines overlaps a part of the display period of the liquid crystal display panel.

8. The detection apparatus according to claim 1, wherein the wavelength selection filter comprises a filter array substrate, a filter counter substrate facing the filter array substrate, and a liquid crystal layer provided between the filter array substrate and the filter counter substrate.

9. The detection apparatus according to claim 1, wherein the photoelectric conversion elements are positive-intrinsic-negative diodes.

10. The detection apparatus according to claim 1, wherein the first light-emitting elements and the second light-emitting elements are inorganic light-emitting elements.

11. The detection apparatus according to claim 1, comprising an optical element that comprises a plurality of light-transmitting areas and a non-light-transmitting area and is provided between the optical sensor and the lighting device, wherein
   the light-transmitting areas are provided so as to penetrate the optical element in a thickness direction in positions overlapping the respective photoelectric conversion elements and are configured to transmit light incident on the photoelectric conversion elements, and the non-light-transmitting area is provided between the light-transmitting areas and has lower light transmittance than that of the light-transmitting areas.

\* \* \* \* \*